US012723235B2

(12) United States Patent
Hui et al.

(10) Patent No.: US 12,723,235 B2
(45) Date of Patent: Sep. 1, 2026

(54) METHOD FOR EXPANDING HEPATOCYTE IN VITRO AND APPLICATION

(71) Applicant: Center for Excellence in Molecular Cell Science, Chinese Academy of Sciences, Shanghai (CN)

(72) Inventors: Lijian Hui, Shanghai (CN); Ludi Zhang, Shanghai (CN); Kun Zhang, Shanghai (CN)

(73) Assignee: Center for Excellence in Molecular Cell Science, Chinese Academy of Sciences, Shanghai (CN)

( * ) Notice: Subject to any disclaimer, the term of this patent is extended or adjusted under 35 U.S.C. 154(b) by 885 days.

(21) Appl. No.: 17/281,161

(22) PCT Filed: Aug. 14, 2019

(86) PCT No.: PCT/CN2019/100511
§ 371 (c)(1),
(2) Date: Mar. 29, 2021

(87) PCT Pub. No.: WO2020/063161
PCT Pub. Date: Apr. 2, 2020

(65) Prior Publication Data

US 2021/0340494 A1 Nov. 4, 2021

(30) Foreign Application Priority Data

Sep. 30, 2018 (CN) ......................... 201811156216.1

(51) Int. Cl.
*A61K 35/407* (2015.01)
*A61P 1/16* (2006.01)
*C12N 5/071* (2010.01)

(52) U.S. Cl.
CPC ............ *C12N 5/067* (2013.01); *A61K 35/407* (2013.01); *A61P 1/16* (2018.01)

(58) Field of Classification Search
CPC .......... C12N 5/067; A61K 35/407; A61P 1/16
See application file for complete search history.

(56) References Cited

U.S. PATENT DOCUMENTS

| | | | | |
|---|---|---|---|---|
| 9,765,301 | B2 * | 9/2017 | Huch Ortega | C12N 5/0672 |
| 10,538,741 | B2 * | 1/2020 | Sokal | A61K 35/407 |
| 2013/0189327 | A1 | 7/2013 | Ortega et al. | |
| 2016/0256672 | A1 * | 9/2016 | Arumugaswami | C12N 5/067 |
| 2017/0107485 | A1 | 4/2017 | Kannemeier et al. | |
| 2017/0191030 | A1 | 7/2017 | Huch Ortega et al. | |
| 2018/0030415 | A1 * | 2/2018 | Nguyen | C12N 5/0672 |

FOREIGN PATENT DOCUMENTS

| | | | |
|---|---|---|---|
| CN | 102459574 | A | 5/2012 |
| CN | 103237888 | A | 8/2013 |
| CN | 107075467 | A | 8/2017 |
| CN | 108431209 | A | 8/2018 |
| WO | 2017048193 | A1 | 3/2017 |
| WO | 2018079714 | A1 | 5/2018 |

OTHER PUBLICATIONS

Garnier D, et al. Expansion of human primary hepatocytes in vitro through their amplification as liver progenitors in a 3D organoid system. Scientific Reports, May 29, 2018; 8:8222; p. 1-10 (Year: 2018).*

Van Wenum M, et al. Oxygen drives hepatocyte differentiation and phenotype stability in liver cell lines. J Cell Commun Signal. Feb. 4, 2018;12(3):575-588. doi:10.1007/s12079-018-0456-4 (Year: 2018).*

Kajiyama Y, Ui M. Differential mitogenic actions of alpha 1- and beta-adrenergic agonists on rat hepatocytes. Cell Signal. Apr. 1998; 10(4):241-51. doi: 10.1016/s0898-6568(97)00122-8. (Year: 1998).*

Roskams T. Different types of liver progenitor cells and their niches. Jour of Hepatology, Jul. 2006; 45(1):1-4. https://doi.org/10.1016/j.jhep.2006.05.002 (Year: 2006).*

Katsuda et al. Conversion of Terminally Commited Hepatocytes to Culturable Bipotent Progenitor Cells with Regerative Capacity. Cell Stem Cell 20, 41-55, Jan. 5, 2017.

Shan et al. “Identification of small molecules for human hepatocyte expansion and iPS differentiation”. Nature Chemical Biology, vol. 9, Aug. 2013.

Ang et al. “A Roadmap for Human Liver Differentiation from Pluripotent Stem Cells”. Cell Reports 22, 2190-2205, Feb. 20, 2018.

Garnier et al. “Expansion of human primary hepatocytes in vitro through their amplification as liver progenitors in a 3D organoid system” Scientific Reports, 2018, 8:8222.

Zhang et al. “In Vitro Expansion of Primary Human Heptocytes with Efficient Liver Repopulation Capacity” Cell Stem Cell 23, 1-14. Dec. 6, 2018.

Suleiman et al. “The effect of oxygen tension on rat hepatocytes in short-term culture” In vitro Cellular & Developmental Biology, vol. 23, No. 5, May 1987.

Huch et al. “Long-term Culture of Genome-Stable Bipotent Stem Cells from Adult Human Liver” Cell 160, 299-312, Jan. 15, 2015.

Wu et al. “Reversible transition between hepatocytes and liver progenitors for in vitro hepatocyte expansion” Cell Research (2017) 27:809-712.

(Continued)

*Primary Examiner* — Peter Paras, Jr.
*Assistant Examiner* — Gillian C. Reglas
(74) *Attorney, Agent, or Firm* — Banner & Witcoff, Ltd.

(57) ABSTRACT

Provided are a method for expanding a hepatocyte in vitro and an application thereof. A culture system is provided for reprogramming a human hepatocyte into a proliferating intermediate-state cell between a mature hepatocyte and a liver progenitor cell. The liver repopulation ability of the system was verified in animals. The method does not require the introduction of an exogenous gene into a hepatocyte, and the expansion of the hepatocyte can be realized by conventional culture. The obtained hepatocyte can be passaged, and can be cultured to maturation to obtain a functional mature human hepatocyte.

6 Claims, 7 Drawing Sheets
(7 of 7 Drawing Sheet(s) Filed in Color)
Specification includes a Sequence Listing.

(56) References Cited

OTHER PUBLICATIONS

Leontieva et al. “Hypoxia suppresses conversion from proliferative arrest to cellular senescence” PNAS 13314-13318, Aug. 14, 2012, vol. 109, No. 33.

* cited by examiner

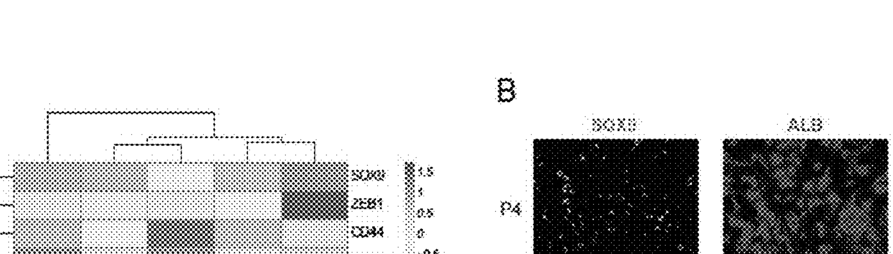
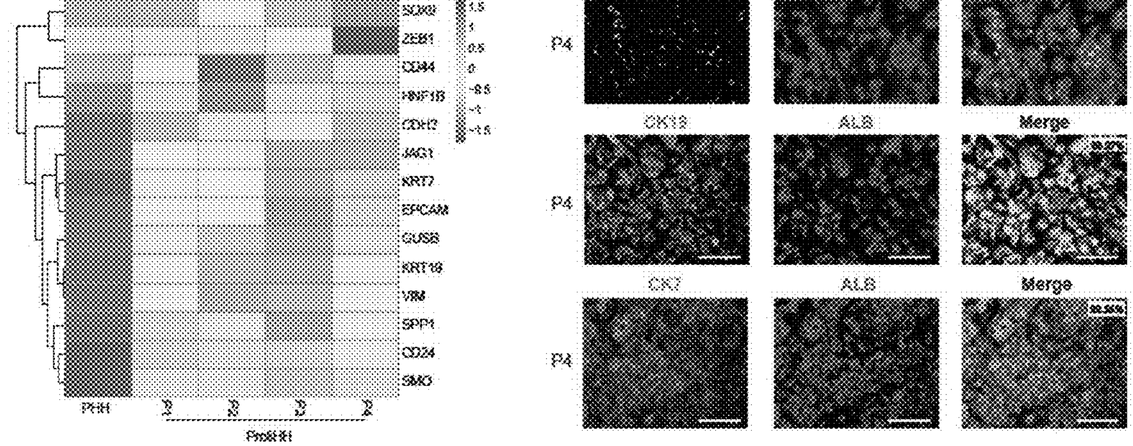
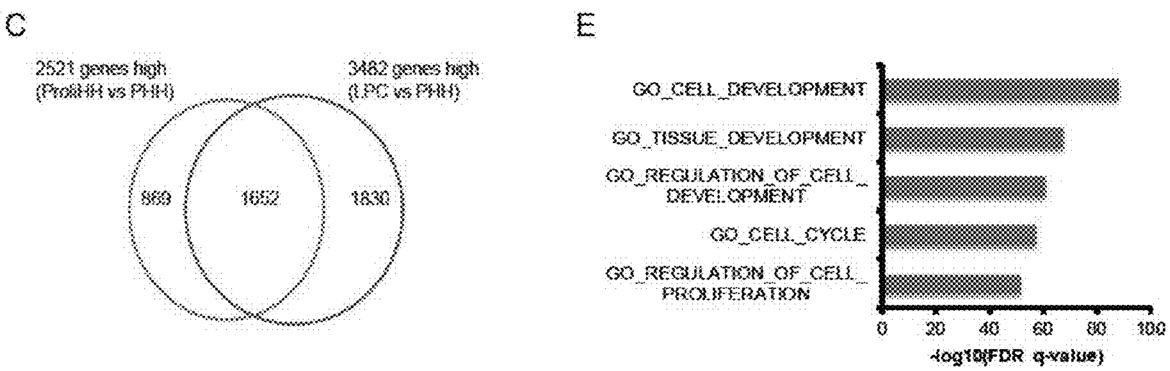
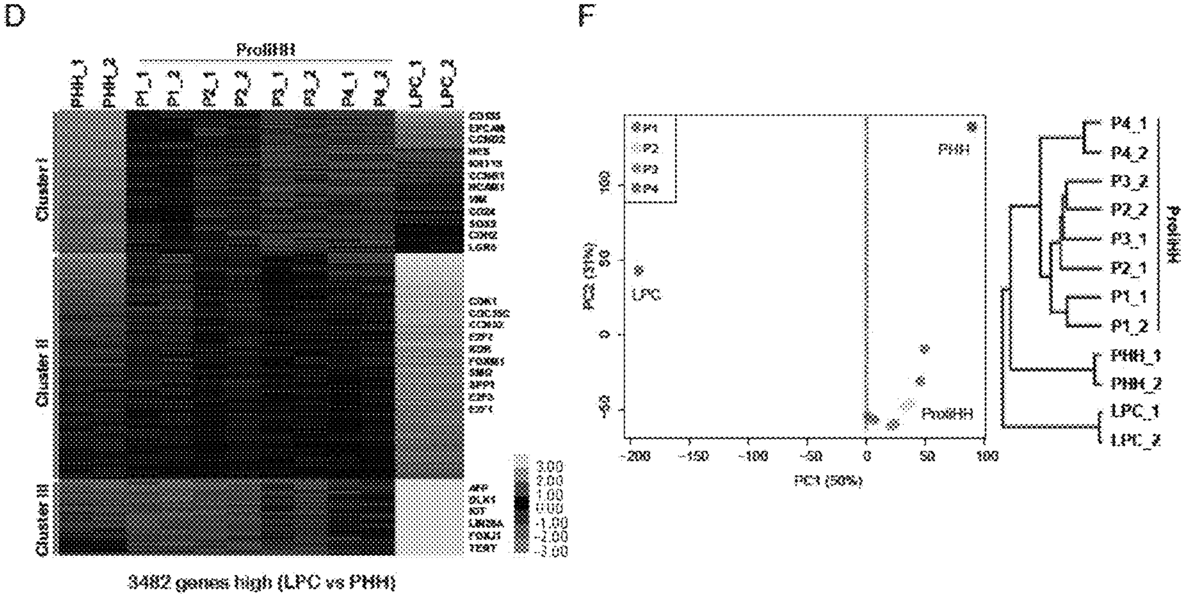
Fig. 4

| | Tumor-bearing mice per injected mice |
|---|---|
| Snu398 | 6/6 |
| ProliHHs | 0/8 |

METHOD FOR EXPANDING HEPATOCYTE IN VITRO AND APPLICATION

FIELD OF DISCLOSURE

The disclosure belongs to the field of biotechnology. More specifically, the disclosure relates to a method for expanding hepatocytes in vitro and the application of metabolic analysis and cell transplantation using the expanded hepatocytes.

RELATED APPLICATIONS

This application is a National Stage Application under 35 U.S.C. 371 of co-pending PCT application number PCT/CN2019/100511 designating the United States and filed Aug. 14, 2019; which claims the benefit of CN application No. 201811156216.1 and filed Sep. 30, 2018 each of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on Mar. 29, 2021, is named "21155251_1.txt" and is 12,208 bytes in size.

BACKGROUND OF DISCLOSURE

Liver is one of the most complex organs with the most functions in the body. Its main functions include: regulating the balance of carbohydrate and lipid, participating in the metabolism and biotransformation of exogenous substances, the generation and excretion of bile, the storage of vitamins, the synthesis of secretory proteins, and the generation and elimination of coagulation substances, playing an important role in specific and non-specific immunity. As the center of metabolism, liver plays an important role in many physiological and pathological processes, and many diseases also affect the liver. At present, the most effective treatment for advanced liver disease is liver transplantation. However, its clinical application is greatly limited due to the limited donor liver and the high cost. In recent years, researchers have tried to replace whole liver transplantation with hepatocyte transplantation, and its effectiveness has been verified in clinical and animal models. However, hepatocyte transplantation is still limited by the lack of human hepatocytes with liver repopulation capability. In addition, due to the specificity of human hepatotropic pathogens to the host and the great differences in liver metabolic enzymes among species, animals with a humanized liver obtained from immunodeficient animals after human hepatocyte transplantation have been widely used in the field of liver infection disease research and drug development. Therefore, human hepatocytes with efficient liver repopulation capability are required and of great value in liver disease treatment and construction of liver-humanized animals.

Cell immortalization refers to the process in which the cells cultured in vitro escape from the senescence crisis spontaneously or by external influence, and thus gain unlimited proliferation ability. The spontaneous immortalization of hepatocytes is extremely rare. Usually, immortalization is achieved by gene transfection or other technologies. However, the in vitro liver function of some immortalized hepatocyte lines is much lower than that of primary hepatocytes, and there is no experiment to prove that they can regenerate (repopulate) in the liver. In addition, some immortalized cells also bring the risk of tumorigenesis in vivo.

The skilled artisan has also adopted co-culture combined with small molecular compounds to promote proliferation of a small amount of human hepatocytes. The advantage of this method is the maintenance of hepatocyte function. However, the cells cannot proliferate many folds, and there is no transplantation experiment to prove that the expanded human hepatocytes have the ability of liver integration. These limit the application of this technology in cell transplantation therapy.

The skilled artisan has also adopted the method of culturing human liver-bile-duct-derived precursor cells as organoids. Although this method has produced liver organoids with the ability of sustainable proliferation, their liver function, even induced, is far inferior to human primary hepatocytes, and their repopulation efficiency after in vivo transplantation is quite low.

The skilled artisan has also dedifferentiated rat hepatocytes into liver progenitor cells in vitro, which achieves large-scale expansion of hepatocytes in vitro and efficient hepatic regeneration after transplantation. However, this technology cannot promote the expansion of human hepatocytes in vitro.

In conclusion, although researchers have made developments in human hepatocyte culture and new mechanisms of liver regeneration, it is impossible for human hepatocytes to proliferate continuously and repopulate efficiently in vivo without gene editing.

SUMMARY OF DISCLOSURE

The purpose of the disclosure is to provide a method and application for expanding a hepatocyte in vitro.

The first aspect of the disclosure provides a method for hepatocytes (including primary hepatocytes) expansion in vitro, comprising: culturing the hepatocytes in a cell culture medium containing a Wnt signaling pathway agonist to expand the hepatocytes in vitro.

In a preferable embodiment, the cell culture medium also contains a component selected from the group consisting of: N-acetylcysteine, nicotinamide, FGF10, EGF, HGF, [Leu15]-Gastin I, A 83-01, Y-27632.

In another preferable embodiment, the Wnt signaling pathway agonist includes an agonist selected from the group consisting of: Wnt3a protein, Wnt3a conditioned medium, CHIR, or a combination thereof.

In another preferable embodiment, the cell culture medium also includes a cell growth supplements selected from the group consisting of: N2 supplement, and neuronal culture supplement sold under the trademark B27™ supplement; or further includes serum.

In another preferable embodiment, the cell culture medium comprises a basal medium selected from the group consisting of: DMEM, MEM, RPMI (such as RPMI1640), Neuronal basal or Fischers; preferably, the DMEM is selected from the group consisting of: Advanced DMEM/F12, and DMEM/F12.

In another preferable embodiment, the method also includes inducing the expanded hepatocytes into mature hepatocytes, including: adding Forskolin, dexamethasone, oncostatin M to the cell culture medium.

In another preferable embodiment, the concentration of the component in the cell culture medium is as follows:

| | |
|---|---|
| Wnt3a protein | 30 to 70 ng/ml, preferably 40 to 60 ng/ml; |
| CHIR | 0.05 to 2 uM, preferably 0.07 to 1.5 uM; |
| N-acetylcysteine | 0.5 to 2 mM, preferably 0.7 to 1.5 mM; |
| Nicotinamide | 5 to 20 mM, preferably 7 to 15 mM; |
| Recombinant human FGF10 | 1 to 4 ng/ml, preferably 2 to 3 ng/ml; |
| Recombinant human EGF | 30 to 70 ng/ml, preferably 40 to 60 ng/ml |
| Recombinant human HGF | 15 to 40 ng/ml, preferably 20 to 30 ng/ml |
| Human [$Leu^{15}$]-gastrin I | 5 to 20 mM, preferably 7 to 15 mM; |
| A 83-01 | 3 to 7 uM, preferably 4 to 6 uM; |
| Y-27632 | 5 to 20 uM, preferably 7 to 15 uM; |
| Forskolin | 3 to 7 uM, preferably 4 to 6 uM; |
| Dexamethasone | 5 to 20 uM , preferably 7 to 15 uM; |
| Oncostatin M(OSM) | 10 to 30 ng/ml, preferably 15 to 25 ng/ml; |
| Serum | 0.5 to 2%, preferably 0.7 to 1.5%. |

In another preferable embodiment, one or a combination of the Wnt3a protein, Wnt3a conditioned medium and CHIR can be selected.

In another preferable embodiment, the amount of the N2 supplement is 1×.

In another preferable embodiment, the amount of the B27™ supplement is 1×.

In another preferable embodiment, the method also includes: sub-culturing the expanded hepatocytes; preferably, the sub-culture is under hypoxic conditions, the hypoxic conditions contain 0-15% oxygen by volume; preferably, less than 10% oxygen, more preferably, less than 6% oxygen, such as 1%, 2%, 3%, 4% oxygen; preferably, the culture is a three-dimensional culture.

In another preferable embodiment, the hepatocytes are human hepatocytes, including human primary hepatocytes.

Another aspect of the present disclosure provides a hepatocyte culture obtained by any of the preceding methods, or hepatocytes isolated (purified) from the hepatocyte culture.

In a preferable embodiment, the hepatocytes are intermediate-state cells between a mature hepatocyte and a liver progenitor cell.

In another preferable embodiment, the hepatocytes are mature hepatocytes; preferably, they have the typical polygonal shape and bi-nuclear of mature hepatocytes, low expression of liver progenitor genes such as Sox9, CK19 or CK7, high expression of key genes involved in drug and urea metabolism, and increased capacity of CYP2B6 and urea metabolism.

Another aspect of the disclosure provides the use of the hepatocyte culture or the isolated hepatocytes in manufacture of a medicament for promoting liver regeneration, in manufacture of a pharmaceutical composition or a kit for preventing, alleviating or treating liver diseases (including liver injury, liver cancer, liver cirrhosis, etc.); as an in vitro model for the research on liver related diseases or drugs; in manufacture of a composition for in vivo cell transplantation; or in production of Albumin protein.

In a preferable embodiment, the research on liver related diseases or drugs includes: research on drug transport, drug metabolism, liver formation and liver regeneration; or hepatotoxicity test, screening of hepatocyte toxic substances and screening of substances regulating hepatocyte function.

In another aspect of the present disclosure, a pharmaceutical composition is provided, comprising the hepatocyte culture or the isolated (purified) hepatocytes; and a pharmaceutically acceptable carrier.

In another aspect of the present disclosure, a pharmaceutical kit is provided, comprising the hepatocyte culture or the isolated (purified) hepatocytes; or the pharmaceutical composition.

In another aspect of the disclosure, a culture medium for hepatocyte expansion in vitro is provided, comprising: Wnt signaling pathway agonist, N-acetylcysteine, nicotinamide, FGF10, EGF, HGF, [Leu15]-gastrin I, A 83-01, Y-27632; wherein the Wnt signaling pathway agonist is selected from the group consisting of: Wnt3a protein, Wnt3a conditioned medium, CHIR, or a combination thereof.

In a preferable embodiment, the medium also includes components selected from the group consisting of: N2 supplement, B27™ supplement and serum.

In another aspect of the disclosure, a culture medium for in vitro expansion of hepatocytes and induction of hepatocyte maturation is provided, comprising: the culture medium for hepatocyte expansion in vitro, Forskolin, dexamethasone and oncostatin M.

In a preferable embodiment, the cell culture medium contains a component selected from the group consisting of: Wnt signaling pathway agonist, N-acetylcysteine, nicotinamide, FGF10, EGF, HGF, [Leu15]-Gastin I, A 83-01, Y-27632.

In another preferable embodiment, the Wnt signaling pathway agonist is selected from the group consisting of: Wnt3a protein, Wnt3a conditioned medium, CHIR, or a combination thereof.

In another preferable embodiment, the medium also includes N2 supplement, B27™ supplement, serum, Forskolin, dexamethasone and oncostatin M.

In another preferable embodiment, each component is in an effective amount.

In another preferable embodiment, the component(s) of cell culture medium is present in a basal medium selected from the group consisting of: DMEM, MEM, RPMI (such as RPMI1640), Neuronal basal or Fischers; preferably, the DMEM is selected from the group consisting of: Advanced DMEM/F12, and DMEM/F12.

In another aspect of the present disclosure, the use of any of the proceeding media is provided for in vitro expansion of hepatocytes and induction of hepatocyte maturation.

In another aspect of the present disclosure, a kit comprising any of the proceeding media is provided, for in vitro expansion of hepatocytes and induction of hepatocyte maturation.

Other aspects of the disclosure will be apparent to those skilled in the art based on the disclosure herein.

BRIEF DESCRIPTION OF DRAWINGS

The patent or application file contains at least one drawing executed in color. Copies of this patent or patent application publication with color drawing(s) will be provided by the Office upon request and payment of the necessary fee. The foregoing and other features and advantages of the present invention will be more fully understood from the following detailed description of illustrative embodiments taken in conjunction with the accompanying drawings in which.

A. Periodic photographs of human hepatocytes cultured in HM medium for 5 days in vitro. Scale, 200 μm.

B. Human hepatocytes were cultured in HM medium for 5 days in vitro. Time-lapse cell confluence was analyzed by IncuCyte FLR.

C. Human hepatocytes were cultured in vitro for 3 days. BrdU and Ki67 cell immunofluorescent staining were used to analyze cell proliferation. Mouse hepatocyte medium YAC was used as negative control. Scale, 100 μm.

D. The senescence of human hepatocytes was analyzed by SA-β-gal staining for the second and fifth passage of normoxic culture, and the sixth passage of hypoxic culture (hypoxia from the first generation).

E. The number of hepatocytes expanded in vitro under hypoxia (hypoxia from the first generation) and normoxia was counted.

F. The number of hepatocytes expanded in vitro from different donors (donor ID: JFC, TVR, DVA, EYP, QIE, XJL, TLY) under hypoxia (hypoxia from the first generation) was counted.

FIG. 2. Wnt3a is necessary for HM medium to promote hepatocyte proliferation.

A. Cell photographs of human hepatocytes cultured for 6 days in: HM medium containing Wnt3a conditioned medium, HM medium without Wnt3a conditioned medium, HM medium containing Wnt3a purified protein instead of Wnt3a conditioned medium, and HM medium containing CHIR instead of Wnt3a conditioned medium.

B. Fold of expansion of human hepatocytes cultured for 6 days in: HM medium containing Wnt3a conditioned medium, HM medium without Wnt3a conditioned medium, HM medium containing Wnt3a purified protein instead of Wnt3a conditioned medium, and HM medium containing CHIR instead of Wnt3a conditioned medium.

Figure 3:
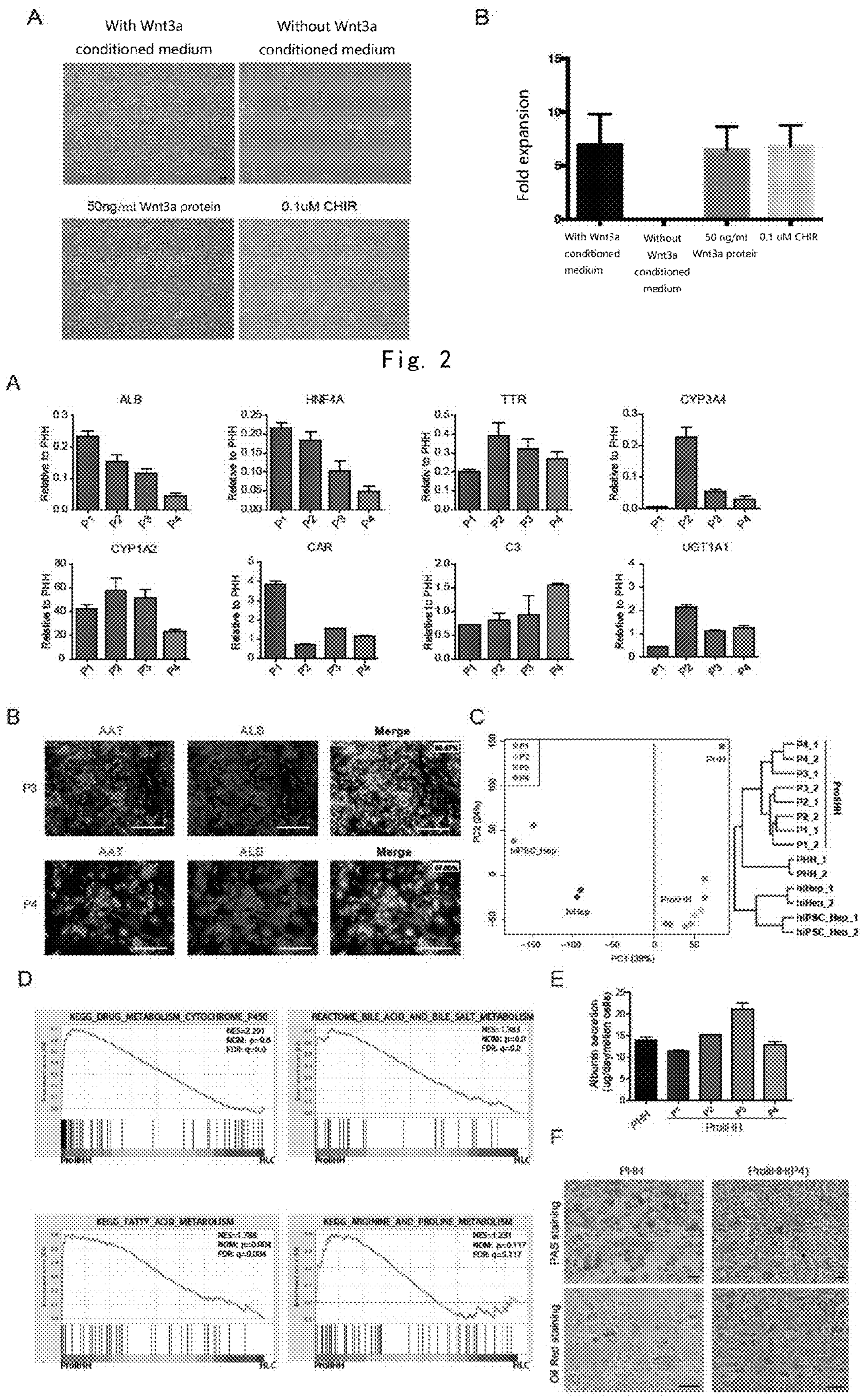

FIG. 3. The proliferating human hepatocytes maintain some function of mature hepatocytes.

A. The expression of hepatocyte genes in human hepatocytes (ProliHH) of different passages. The data was normalized with the expression level of primary human hepatocytes (PHH) as 1. P1 to P4 represent the first to fourth generations (passages).

B. Immunofluorescent co-localization staining of ProliHHs by ALB and AAT. Scale, 100 μm.

C. Principal component analysis and cluster analysis were used to analyze the whole genome expression profiles of ProliHH, PHH, hiHep and hiPSC-Hep.

D. Gene set enrichment analysis (GSEA) was used to identify the gene pathway enriched in ProliHHs relative to PHH.

E. ELISA was used to analyze the secretion of human albumin of different generations of ProliHH.

F. Periodic acid-Schiff staining and oil red staining were used to identify the glycogen storage capacity and lipid droplet accumulation capacity of the 4th generation ProliHH, respectively.

FIG. 4. The proliferating human hepatocytes are in the intermediate-state between mature hepatocytes and liver progenitor cells.

A. The expression of characteristic genes of liver progenitor cells in ProliHHs and PHHs was analyzed based on the results of RNA sequencing.

B. Immunofluorescent co-localization staining of ProliHHs by ALB, CK19, CK7 and SOX9. Scale, 100 um.

C. The number and intersection of the genes whose expression in ProliHHs and LPCs is up-regulated (>=3 fold up-regulation) relative to PHHs were analyzed by Venn diagram.

D. Cluster analysis of the expression of LPC-enriched genes in PHHs, ProliHHs and LPCs.

E. Gene set enrichment analysis (GSEA) was used to identify the signal pathways enriched in LPC-enriched gene sets I and II.

F. Principal component analysis and cluster analysis were used to analyze the whole genome expression profiles of ProliHH, PHH, hiHep and hiPSC-Hep.

Figure 5:
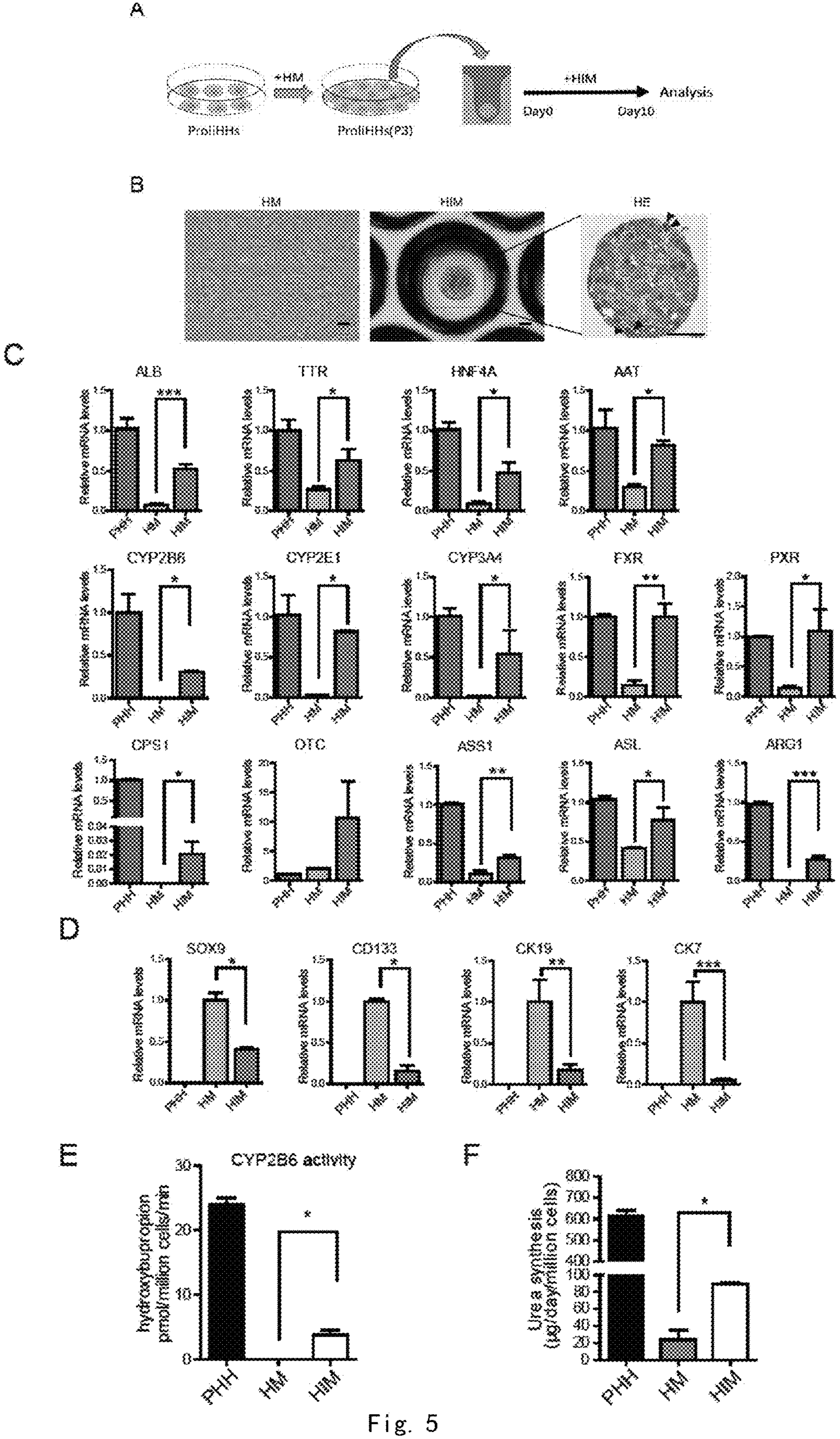

FIG. 5. Proliferating human hepatocytes can be induced into mature hepatocytes in vitro.

A. Flow chart of in vitro induction of ProliHHs maturation. ProliHHs was cultured and proliferating with HM, and then induced to hepatic maturation by HIM combined with 3D culture conditions in vitro.

B. Representative images of ProliHHs without in vitro induced maturation and ProliHH liver organoids after in vitro 3D induced maturation. Black arrows indicate binuclei cells. Scale, 100 μm.

C. Expression of hepatocyte genes in ProliHHs after 10 days of in vitro hepatic maturation induction. The data was normalized with the expression level of primary human hepatocytes (PHH) as 1.

D. Expression of liver progenitor cell genes in ProliHHs after 10 days of in vitro hepatic maturation induction. The data was normalized with the expression level of ProliHHs cultured in HM as 1.

E. The CYP2B6 metabolic activity of ProliHHs after in vitro induced maturation was detected by analyzing metabolic products of hydroxybupropion by liquid chromatography-tandem mass spectrometry. PHHs were used as a positive control.

F. Detection of urea metabolism ability of ProliHHs after in vitro induced maturation.

Figure 6:
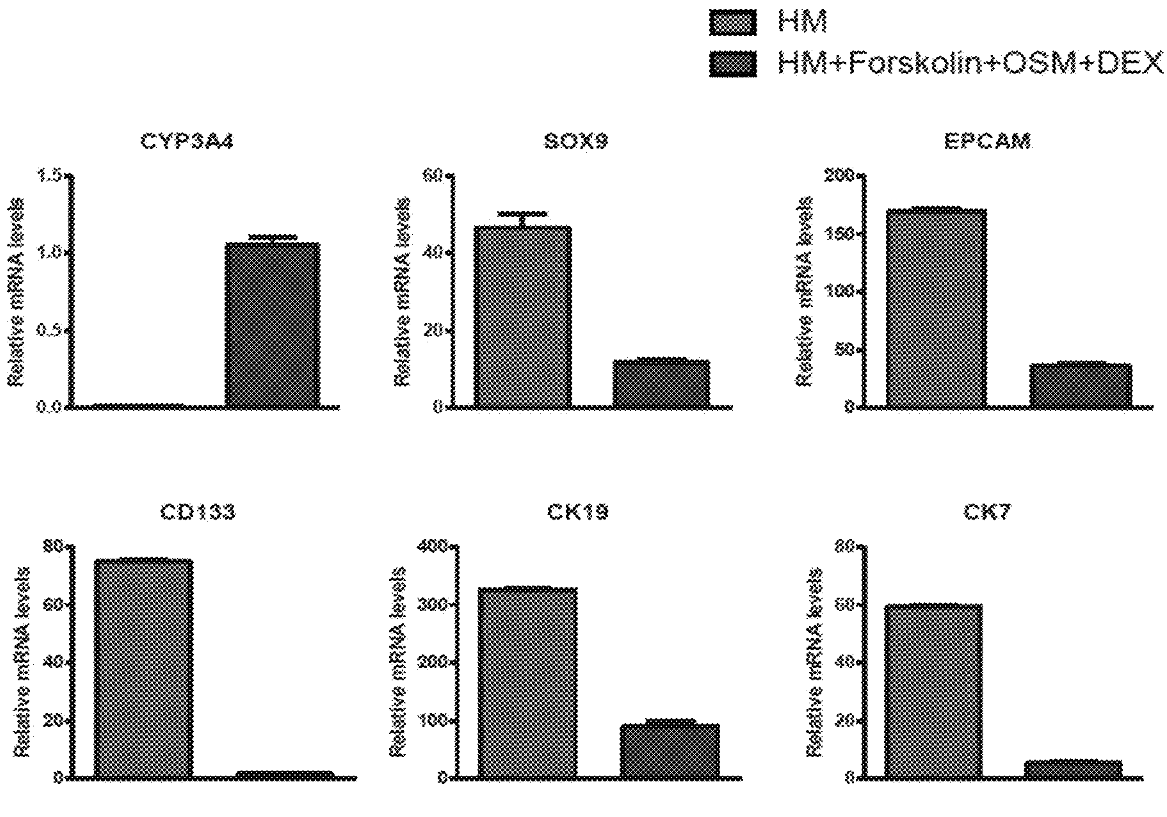

FIG. 6. Identification of key factors in HIM that promote hepatocyte maturation. The expanded hepatocytes ProliHHs were placed in 3D culture conditions to form liver organoids, which were cultured with HM and HIM, respectively. Quantitative PCR was used to detect the expression of liver cell gene CYP3A4 (key metabolic gene) and liver progenitor genes SOX9, EPCAM, CD133, CK19, CK7.

Figure 7:
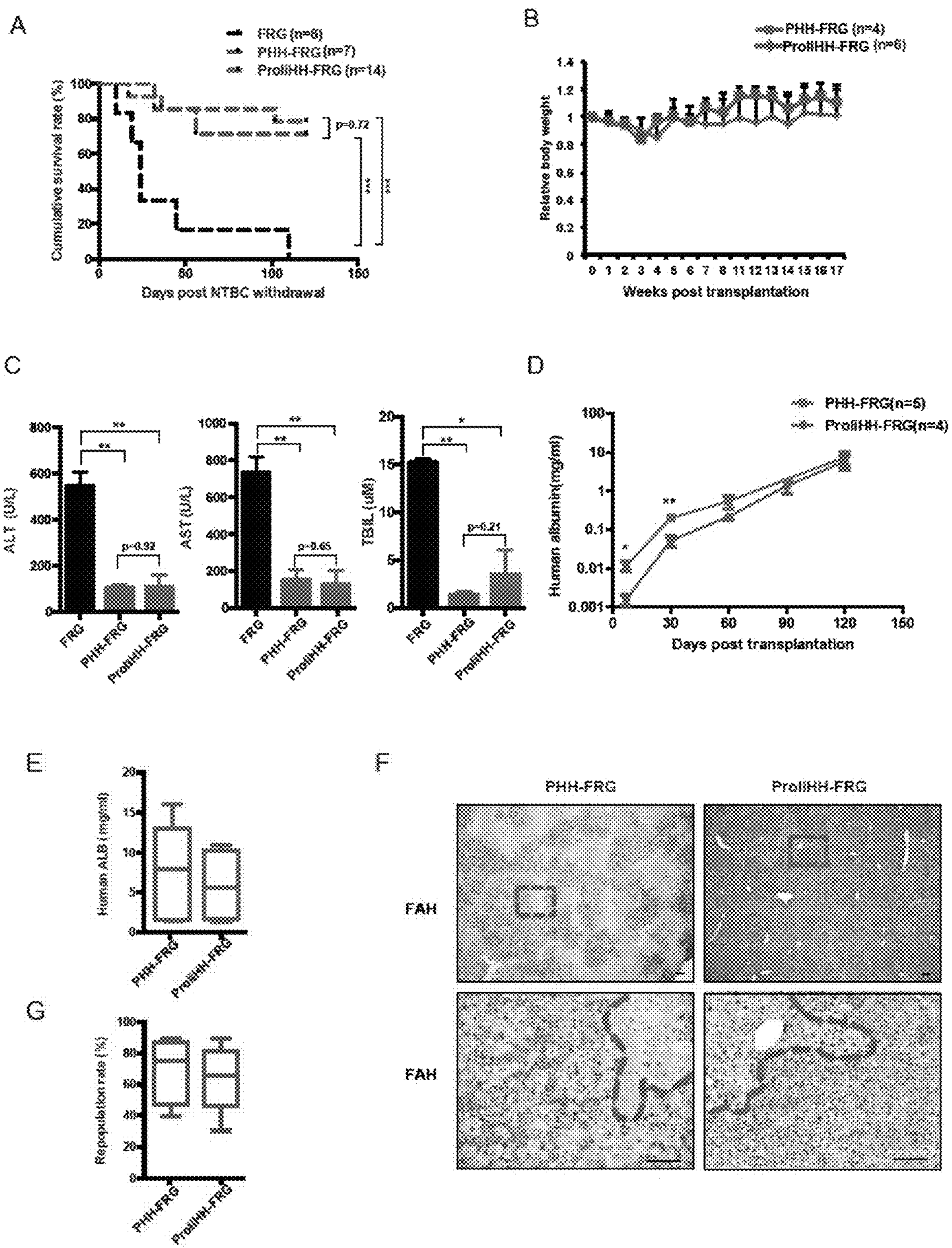

FIG. 7. Proliferating human hepatocytes can be induced into mature hepatocytes in vitro.

A. Kaplan-Meier survival curves of none-transplanted FRG mice and FRG mice transplanted with ProliHHs and PHHs.

B. The body weight curves of FRG mice after transplantation of ProliHHs (n=6) and PHHs (n=4).

C. Serum levels of ALT, AST and TBIL in FRG mice that were dying without transplanted cells (n=3), FRG mice transplanted with ProliHHs (n=3), and FRG mice transplanted with PHHs (n=4).

D. ELISA was used to detect the dynamic changes of human albumin in FRG serum after transplantation of ProliHHs (n=4) and PHHs (n=5).

E. The amount of human albumin in the serum of mice survived for 4 months after transplantation of ProliHHs (n=4) and PHHs (n=5).

F. Fah immunohistochemical staining of the livers of mice survived for 4 months after transplantation of ProliHHs and PHHs.

G. Quantitative analysis of the repopulation efficiency of ProliHHs and PHHs in FRG liver by Fah immunohistochemical staining.

Figures 8, 9:
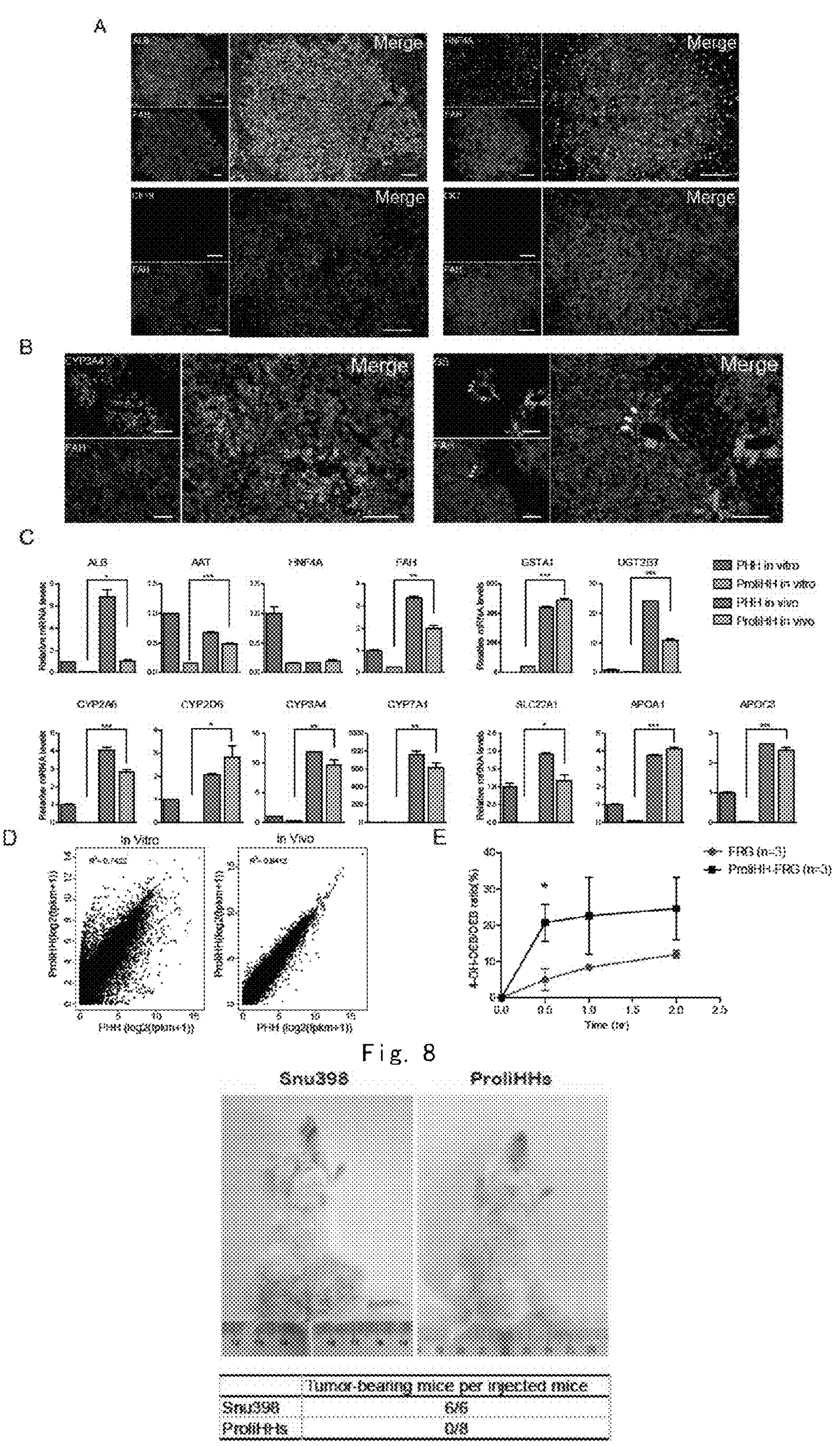

FIG. 8. After transplantation, the liver function of the proliferating human hepatocytes is fully mature in vivo.

A. ProliHHs repopulated in vivo were subjected to immunofluorescent co-localization staining for Fah, ALB, HNF4a, CK19 and CK7.

B, Fah, CYP3A4 and GS immunofluorescence co-localization staining was used to analyze the zonation expression of liver metabolism genes.

C. Comparison of the expression of mature hepatocyte functional genes such as phase I and phase II metabolic enzymes and transporters in PHHs and ProliHHs in vitro and PHHs and ProliHHs repopulated in vivo.

D. Similarity analysis of the whole genome expression profile of PHHs and ProliHHs in vitro and PHHs and ProliHHs repopulated in vivo.

E. FRG mice transplanted with ProliHHs were analyzed for human specific CYP2D6 drug metabolism. Control FRG mice (n=3) and FRG mice transplanted with ProliHHs (n=3) were tested for serum DEB and 4-OH DEB concentrations 0-2 hours after injection of 2 mg/kg DEB.

FIG. 9. The proliferating human hepatocytes do not have a risk of tumorigenesis in vivo. $2\times10^6$ ProliHHs (n=8) and liver cancer cell line Snu-398 (n=6) were injected subcutaneously into the groin of NOD-SCID mice with severe immunodeficiency, and tumor formation was assayed two months later.

DETAILED DESCRIPTION

On the basis of the flexibility of human hepatocytes in regeneration, the inventor established a culture system for reprogramming human hepatocytes into proliferative intermediate-state cells between mature hepatocytes and liver progenitor cells. The method does not require the introduction of an exogenous gene into a hepatocyte, and the expansion of the hepatocyte can be realized by conventional culture. The obtained hepatocyte can be passaged, and can be cultured to maturation to obtain a functional mature human hepatocyte. In addition, the method requires simple cultivation conditions and low cost, and is safety and stability.

As used herein, the term "comprising" or "including" includes "containing", "consisting (made) mainly of", "consisting essentially of" and "consisting of".

Unless otherwise specified, the objects of culture in the present disclosure are hepatocytes, particularly primary hepatocytes, more particularly human hepatocytes or human primary hepatocytes.

Culture Method

The present disclosure discloses a method for in vitro hepatocyte expansion: the hepatocytes are cultured in the "hepatocyte medium (in vitro expansion medium)" of the present disclosure to obtain a large amount of intermediate-state hepatocytes between mature hepatocytes and liver progenitor cells. In some embodiments of the present disclosure, it is observed that the intermediate-state hepatocytes express liver progenitor cell-associated markers SOX9, CK19 and CK7, present lower expression levels of ALB, HNF4A, TTR or CYP3A4 than that of primary hepatocytes, and present similar or higher expression levels of CYP1A2, CAR, C3 or UGT1A1 than that of primary hepatocytes. These cells can be further induced into mature hepatocytes.

The method for in vitro hepatocyte expansion includes: culturing hepatocytes in a cell culture medium containing a Wnt signaling pathway agonist to expand the hepatocytes in vitro. The Wnt signaling pathway agonist includes an agonist selected from the group consisting of: Wnt3a protein, Wnt3a conditioned medium, CHIR, or a combination thereof. The Wnt signal pathway agonist is a key factor of the method herein. The experimental results show that, without the Wnt signaling pathway agonist, the medium could not provide good cell expansion.

In a preferable embodiment, the cell culture medium also contains a component selected from the group consisting of: N-acetylcysteine, nicotinamide, FGF10, EGF, HGF, [Leu15]-Gastin I, A 83-01, Y-27632, N2 supplement, B27™ supplement, serum. In the most preferable embodiment, the cell culture medium contains all the above-mentioned components.

In a preferable embodiment, the method also comprises a step of inducing the expanded hepatocytes into mature hepatocytes, including: culturing the cells in the "hepatocyte induction medium (hepatic maturation medium)" of the present disclosure. Compared with the in vitro expansion medium, the hepatic maturation medium further comprises Forskolin, dexamethasone, oncostatin M. In some embodiments, the hepatocytes have the typical polygonal shape and bi-nuclear of mature hepatocytes, low expression of liver progenitor genes such as SOX9, CK19 or CK7, high expression of key genes involved in drug and urea metabolism, and increased capacity of CYP2B6 and urea metabolism.

The inventor unexpectedly discovered that hypoxia treatment increases the generation of hepatocytes cultured in the present disclosure. Therefore, in the preferable embodiment of the present disclosure, sub-culturing cells under hypoxic conditions, the hypoxic conditions contain 0-15% oxygen by volume; preferably, less than 10% oxygen, more preferably, less than 6% oxygen.

The culture method and culture medium of the present disclosure can be applied in a two-dimensional or three-dimensional culture system. As a preferable embodiment of the present disclosure, the culture is a three-dimensional culture.

The mature hepatocytes obtained by the method of the present disclosure can be cryopreserved, resuscitated, passaged, and maintained in culture for a long time. In addition, it should also be understood that the hepatocytes (primary hepatocytes) used as the initial strain in the present disclosure may be established primary hepatocytes, or may be hepatocytes isolated from organisms.

Culture Medium

The inventor provides a medium for expanding hepatocytes in vitro. The medium includes "in vitro expansion medium" and "hepatic maturation medium".

The in vitro expansion medium includes: a Wnt signaling pathway agonist, and a component selected from the group consisting of N-acetylcysteine, nicotinamide, FGF10, EGF, HGF, [Leu15]-gastrin I, A 83-01, Y-27632, N2 supplement, B27™ supplement, serum. The medium can proliferate hepatocytes quite well.

The hepatic maturation medium is the in vitro expansion medium added with Forskolin, dexamethasone, and oncostatin M.

It should be understood that any agonist that can activate the Wnt signaling pathway other than the particular Wnt signaling pathway agonists listed in the embodiments herein can also achieve the same technical effect and should also be included in the present disclosure. Preferably, the Wnt signaling pathway agonist includes an agonist selected from the group consisting of: Wnt3a protein, Wnt3a conditioned medium, CHIR, or a combination thereof.

Similarly, analogs, homo-functional proteins (such as the homo-functional proteins of growth factors) or homo-functional compounds of the above-listed components; equivalent compounds, analogs, or derivatives that induce the same target, and/or salts, hydrates or precursors thereof, can be used to replace the above-listed components to achieve the same technical effect. These analogs, homo-functional proteins or compounds should also be included in the present disclosure. Compound analogs include, but are not limited to: isomers or racemates of the compounds. Compounds have one or more asymmetric centers. Therefore, these compounds can be present as racemic mixtures, individual enantiomers, individual diastereomers, mixtures of diastereomers, cis- or trans-isomers. The "salts" include but are not limited to: (1) salts formed with the following inorganic acids: such as hydrochloric acid, sulfuric acid, nitric acid, or phosphoric acid, etc.; (2) salts formed with the following organic acids: such as acetic acid, oxalic acid, succinic acid, tartaric acid, methanesulfonic acid, maleic acid, or arginine, etc. Other salts include salts formed with alkali metals or alkaline earth metals (such as sodium, potassium, calcium, or magnesium). The "compound precursor" refers to a compound that, when applied or treated by an appropriate method, can be converted into any of the above-mentioned compounds in the culture medium, or to the salt or solution of any of the above-mentioned compounds.

As a preferable embodiment herein, the medium is also added with component(s) that prevents bacterial contamination during cell culture, especially Gram-positive and -negative bacterial contamination. Preferably, penicillin is added (such as 1%; and the percentage numeral is meant to cover 50% fluctuations, preferably 30% fluctuations; more preferably 20% fluctuations, such as 10%, 5% fluctuations).

The basal cell culture medium can be, but is not limited to: DMEM/F12, MEM, DMEM, RPMI1640, Neuronal basal or Fischers, etc. It should be understood that those skilled in the art are familiar with the preparation or purchase of the basal cell culture medium. Therefore, the basal cell culture medium is not limited to those exemplified in the present disclosure.

The present disclosure also provides a kit, which contains the "in vitro expansion medium" or "hepatic maturation medium" of the present disclosure. Preferably, the kit also contains instructions for use, so that it is convenient for those skilled in the art to apply it in research or clinically.

Cultured Hepatocytes and Composition

On the basis of inventor's discovery, a hepatocyte culture obtained by the method of the present disclosure or hepatocytes isolated from the hepatocyte culture is provided, the hepatocytes including those intermediate-state cells between mature hepatocytes and liver progenitor cells, or mature hepatocytes following further induction.

The method of enriching or isolating (purifying) cells from cell culture is well known to those skilled in the art. For example, enrichment can be conducted according to the epithelial morphological characteristics of hepatocytes, or selection and collection can be conducted based on special proteins expressed by hepatocytes (such as Albumin) or molecular markers (for example, by specific antibodies or ligands). In addition, it is also feasible to enrich hepatocytes by removing (such as digesting or lysing) other cells with non-epithelial morphology. As an optional embodiment, flow cytometry can be used to separate cells through a molecular marker on hepatocyte surface.

The hepatocytes cultured in the present disclosure have many uses, including but not limited to: use in manufacture of a composition (pharmaceutical composition) for promoting liver regeneration; use in manufacture of a pharmaceutical composition or a composition (pharmaceutical composition) for treatment of liver injury (including but not limited to: end-stage liver disease, cirrhosis, alcoholic liver, diabetes, obesity, acute liver failure, hepatitis, liver fibrosis, liver cancer, liver metabolic disease or liver damage caused by liver failure); use as an in vitro model for a research on liver-related diseases or drug efficacy (such as the research on drug transport, drug metabolism, liver formation and liver regeneration, hepatotoxicity test, screening of hepatocyte toxic substances and screening of substances regulating hepatocyte function); or in production of Albumin protein; etc.

The hepatocytes cultured in the present disclosure can be used in liver toxicology research, and can also be used in liver disease treatment by cell transplantation, bio-artificial liver construction, liver toxicity detection of new drugs, drug efficacy evaluation, drug target identification; it can provide sufficient hepatocyte sources or hepatocyte models for basic research in biology, medicine and pharmacy and clinical applications; its induced differentiation process can also provide an optimal platform for the research on development and differentiation of human liver cells. It has broad promising applications.

If needed, the cultured hepatocytes herein can be further applied to genetic engineering to form recombined cells, in order to, for example, impart further functions or characteristics to the cells, transfer exogenous gene cassettes into the cells, or knock out or edit genes of the cell genome.

The present disclosure also provides a composition (medicament) comprising: an effective amount of the hepatocytes (such as $1*10^4$-$1*10^{12}$; preferably $1*10^5$-$1*10^{10}$), and a pharmaceutically acceptable carrier. It comprises an effective amount of the hepatocytes and a pharmaceutically acceptable carrier. The composition has no detectable toxicity or side effects to animals.

The "effective amount" refers to an amount that can produce function or activity on humans and/or animals and can be accepted by the humans and/or animals. The "pharmaceutically acceptable carrier" refers to a carrier used for the administration of a therapeutic agent, and includes various excipients and diluents. The term refers to pharmaceutical carriers that are not essential active ingredients in themselves and do not cause excessive toxicity after administration. Suitable carriers are well known to those of ordinary skill in the art. The pharmaceutically acceptable carrier in the composition may contain liquid, such as water, saline, and buffer. In addition, these carriers may also contain auxiliary substances, such as fillers, lubricants, glidants, wetting agents or emulsifiers, pH buffer substances. The carriers may also contain a cell transfection reagent.

The present disclosure also provides a method for promoting liver regeneration, comprising: administering to a subject in need an effective amount of hepatocytes cultured in the present disclosure.

The composition is administrated usually at $1*10^2$-$1*10^{10}$ cells/kg body weight, preferably at $1*10^3$-$1*10^8$ cells/kg body weight. It also depends on the clinician's diagnosis and the severity of the patient's symptoms.

The present disclosure also provides a kit, which contains the hepatocytes cultured in the present disclosure or a composition containing the hepatocytes. Preferably, the kit also contains instructions for use, so that it is convenient for those skilled in the art to apply it in research or clinically.

The disclosure is further illustrated by the specific examples described below. It should be understood that these examples are merely illustrative, and do not limit the scope of the present disclosure. The experimental methods without specifying the specific conditions in the following examples generally used the conventional conditions, such as those described in J. Sambrook, Molecular Cloning: A Laboratory Manual (3rd ed. *Science Press,* 2002) or followed the manufacturer's recommendation.

Materials and Methods

1. Experimental Materials 1.1. Hepatocyte Medium

The components of hepatocyte medium and their sources (in vitro expansion medium, HM) are shown in Table 1. The working concentration of each component is the final concentration in the culture medium.

TABLE 1

| Hepatocyte medium components | Working concentration | Company |
|---|---|---|
| Advanced DMEM/F-12 | 1X | Life Technologies |
| N2 supplement 100x | 1X | Life Technologies |
| B27 ™ Supplement 50x, minus vitamin A | 1X | Life Technologies |
| N-acetylcysteine | 1 mM | Sigma-Aldrich |
| Nicotinamide | 10 mM | Solarbio |
| Recombinant human FGF10 | 2 ng/ml | Peprotech |
| Recombinant human EGF | 50 ng/ml | Peprotech |
| Recombinant human HGF | 25 ng/ml | Peprotech |
| human [Leu15]-gastrin I | 10 mM | Sigma-Aldrich |
| A 83-01 | 5 uM | Tocris Bioscience |
| Rho kinase inhibitor Y-27632 | 10 uM | Selleck |
| Wnt3a protein*(or 30% Wnt3a conditioned medium) | 50 ng/ml | stemimmune LLC |
| Bovine Serum | 1% | Ausbian |
| Penicillin Streptomycin | 1X | Solarbio |

*This component can be replaced by 30% Wnt3a conditioned medium or 0.1 uM CHIR. The Wnt3a conditioned medium was the culture supernatant produced by the L-Wnt3a cell line (obtained from Hans Clevers laboratory of Hubrecht Institute) after two days of culture.

1.2. Hepatocyte Induction Medium

The components of hepatocyte induction medium and their sources (hepatic maturation medium, HIM) are shown in Table 2. The working concentration of each component is the final concentration in the culture medium.

TABLE 2

| Hepatocyte induction medium components | Working concentration | Company |
|---|---|---|
| Advanced DMEM/F-12 | 1X | Life Technologies |
| N2 supplement 100x | 1X | Life Technologies |
| B27 ™ Supplement 50x, minus vitamin A | 1X | Life Technologies |
| N-acetylcysteine | 1 mM | Sigma-Aldrich |
| Nicotinamide | 10 mM | Solarbio |
| Recombinant human FGF10 | 2 ng/ml | Peprotech |
| Recombinant human EGF | 50 ng/ml | Peprotech |
| Recombinant human HGF | 25 ng/ml | Peprotech |
| Human [$Leu^{15}$]-gastrin I | 10 mM | Sigma-Aldrich |
| A 83-01 | 5 uM | Tocris Bioscience |
| Y-27632 | 10 uM | Selleck |
| Wnt3a Protein* | 50 ng/ml | stemimmune LLC |
| Forskolin | 5 uM | Tocris Bioscience |
| Dexamethasone(DEX) | 10 μM | Sigma-Aldrich |
| Oncostatin M(OSM) | 20 ng/ml | Peprotech |
| Bovine Serum | 1% | Ausbian |
| Penicillin Streptomycin | 1% | Solarbio |

*This component can be replaced by 30% Wnt3a conditioned medium or 0.1 uM CHIR (CHIR99021). The Wnt3a conditioned medium was the culture supernatant produced by the L-Wnt3a cell line (obtained from Hans Clevers laboratory) after two days of culture.

1.3 Control Medium: Medium YAC

The components of control YAC:

| YAC components | Concentration | Company |
|---|---|---|
| DMEM/F12 | 1X | Life Technologies |
| $NaHCO_3$ | 2.4 g/L | BIO BASIC INC |
| L-glutamine | 2.4 g/L | Dingguo |
| HEPES | 5 mM | Solarbio |
| L-proline | 30 mg/L | Solarbio |
| BSA | 0.05% | Solarbio |
| EGF | 40 ng/ml | Peprotech |
| Insulin-transferrin-sodium selenite media supplement | 1X | lifetech |
| Dexamethasone | 0.1 uM | Sigma-Aldrich |
| Nicotinamide | 10 mM | Solarbio |
| Ascorbic acid-2 phosphate | 1 mM | Sigma |
| Penicillin-Streptomycin | 0.01 | Solarbio |
| Y-27632 | 10 uM | Selleck |
| A-83-01 | 0.5 mM | Tocris Bioscience |
| CHIR99021 | 3 mM | Axon Medchem |

1.4 Cell

Different batches of human hepatocytes were purchased from Celsis In Vitro Technologies (Baltimore, MD, U.S). L-Wnt3a cell line was obtained from Hans Clevers laboratory. Snu-398 cell line was purchased from ATCC (U.S).

1.5 Animal $Fah^{-/-}Rag2^{-/-}IL2rg^{-/-}$(FRG) mice: fumarylacetoacetate hydrolase (FAH) gene knockout mice (abbreviated as $Fah^{-/-}$ mice) were established in 1993. Fah/mice accumulate succinyl in the liver due to the lack of complete tyrosine metabolism, resulting in the death of hepatocytes. $Fah^{-/-}$ mice fed with drinking water containing NTBC have no obvious difference in phenotype from wild-type mice, have normal liver function and can develop and reproduce normally. However, they will die of liver failure within 4-6 weeks after stopping NTBC feeding. $Fah^{-/-}$ mice have extensive and continuous liver injury, and their liver microenvironment is particularly suitable for the proliferation of transplanted cells. The liver of $Fah^{-/-}$ mice can be almost completely (more than 90%) reconstructed after spleen transplantation of wild hepatocytes (with normal FAH gene expression), and the recipient mice restored normal liver function. After crossing $Fah^{-/-}$ mice and $Rag2^{-/-}IL2rg^{-/-}$ immunodeficient mice, $Fah^{-/-}Rag2^{-/-}IL2rg^{-/-}$ mice (FRG mice) with the three gene knockouts were obtained. FRG mice lack mature T, B cells and NK cells. After being transplanted with human hepatocytes, the mice can repopulate a high degree (>90%) of human hepatocytes.

2. Experimental Method 2.1 Human Hepatocyte Culture

Cryopreserved human liver cells were purchased from Celsis In Vitro Technologies (Baltimore, MD, U.S.). The cryopreserved human hepatocytes were resuscitated in DMEM medium containing 10% serum, and seeded in a collagen-I-coated plate at $2*10^4$ cells/$cm^2$. The culture plate was incubated at 37° C. in a 5% $CO_2$, 5% $O_2$ incubator. The medium was changed to the hepatocyte medium one day after seeding and every 3 days thereafter. After 6 days of culture, the fully grown cells were trypsinized and seeded in a collagen-I-coated plate at $3*10^4$ cells/$cm^2$. The culture plate was incubated at 37° C. in a 5% $CO_2$ and 5% $O_2$ incubator.

2.2 Hepatic Induction Experiment of Proliferating Hepatocytes

The fully grown proliferating human hepatocytes are trypsinized and re-suspended in the hepatocyte medium, and seeded in a non-attached 24-well plate (Elplasia, Japan) at $5*10^5$ cells/well. One day later, the medium was replaced with the hepatocyte induction medium, and the cells will slowly aggregate into cell spheres. The medium was changed every 2 days, and the induced cells were collected 10 days after the induction.

2.3 Cell Culture and Photography

The cryopreserved human hepatocytes were resuscitated in DMEM supplemented with 10% serum, and seeded in a collagen-I-coated dish at a $2*10^4$ cells/$cm^2$. After the cells were adhered, the medium was changed to hepatocyte medium, and the cell plate was placed in the 37° C., 5% CO2 incubator of incuCyte FLR. The cells were cultured for 3 days, and photographed every 30 minutes under the same field of view. The video of cell culture and proliferation was generated by the software.

2.4 Gene Expression Assay

1) Extract cellular RNA by Trizol (Invitrogen) or RNeasy FFPE Kit (Qiagen).

2) Obtain cDNA by M-MLV reverse transcriptase (Promega) kit, using 1 μg Trizol-extracted RNA, or 1 μg or all (according to the particular amount) of the RNA extracted by RNeasy FFPE Kit.

3) Perform real-time quantitative PCR using SYBR Premix Ex Taq kit (TaKaRa), and detect expression of genes with ABI StepOnePlus real-time PCR system (Applied Biosystems). All Q-PCR data were performed with at least 2 repeats. Primer sequences are shown in Table 3.

TABLE 3

| Gene | Forward (5'-3') | Reverse (5'-3') |
|---|---|---|
| ALB | GCCTTTGCTCAGTATCTT(SEQ ID NO: 1) | AGGTTTGGGTTGTCATCT(SEQ ID NO: 2) |
| AAT | TATGATGAAGCGTTTAGGC(SEQ ID NO: 3) | CAGTAATGGACAGTTTGGGT(SEQ ID NO: 4) |
| TTR | TGGGAGCCATTTGCCTCTG(SEQ ID NO: 5) | AGCCGTGGTGGAATAGGAGTA(SEQ ID NO: 6) |
| CYP1A2 | CTTCGCTACCTGCCTAACCC(SEQ ID NO: 7) | GACTGTGTCAAATCCTGCTCC(SEQ ID NO: 8) |
| CYP2A6 | CAGCACTTCCTGAATGAG(SEQ ID NO: 9) | AGGTGACTGGGAGGACTTGAGGC(SEQ ID NO: 10) |
| CYP2B6 | GCACTCCTCACAGGACTCTTG(SEQ ID NO: 11) | CCCAGGTGTACCGTGAAGAC(SEQ ID NO: 12) |
| CYP2D6 | TGAAGGATGAGGCCGTCTGGGAGA(SEQ ID NO: 13) | CAGTGGGCACCGAGAAGCTGAAGT(SEQ ID NO: 14) |
| CYP3A4 | TTCAGCAAGAAGAACAAGGACAA(SEQ ID NO: 15) | GGTTGAAGAAGTCCTCCTAAGC(SEQ ID NO: 16) |
| CYP7A1 | AGAAGCATTGACCCGATGGAT(SEQ ID NO: 17) | AGCGGTCTTTGAGTTAGAGGA(SEQ ID NO: 18) |
| CAR | GTGCTCCTGTGCGGAGTAG(SEQ ID NO: 19) | ATGGCAGATAGGCAGTTTCCC(SEQ ID NO: 20) |
| PXR | AAGCCCAGTGTCAACGCAG(SEQ ID NO: 21) | GGGTCTTCCGGGTGATCTC(SEQ ID NO: 22) |
| FXR | AACCATACTCGCAATACAGCAA(SEQ ID NO: 23) | ACAGCTCATCCCCTTTGATCC(SEQ ID NO: 24) |
| APOB | CAGCTGATTGAGGTGTCCAG(SEQ ID NO: 25) | CACTGGAGGATGTGAGTGGA(SEQ ID NO: 26) |
| FAH | CCTACGGCGTCTTCTCGAC(SEQ ID NO: 27) | CTGCAAGAACACTCTCGCCT(SEQ ID NO: 28) |
| AFP | ACTGAATCCAGAACACTGCA(SEQ ID NO: 29) | TGCAGTCAATGCATCTTTCA(SEQ ID NO: 30) |
| GAPDH | CCACCTTTGACGCTGGG(SEQ ID NO: 31) | CATACCAGGAAATGAGCTTGACA(SEQ ID NO: 32) |
| EPCAM | AGGAGATGGGTGAGATGC(SEQ ID NO: 33) | GATTGGTAAAGCCAGTTTC(SEQ ID NO: 34) |
| LGR5 | TCCACTTTGCCATCCCTAA(SEQ ID NO: 35) | GGTCGTCCATACTGCTGTTG(SEQ ID NO: 36) |
| CFTR | TGAAACTGACTCGGAAGG(SEQ ID NO: 37) | CAGAATGAGATGGTGGTG(SEQ ID NO: 38) |
| CK19 | TCCGAACCAAGTTTGAGACG(SEQ ID NO: 39) | CCCTCAGCGTACTGATTTCCT(SEQ ID NO: 40) |
| SOX9 | GACTACACCGACCACCAGAACTCC(SEQ ID NO: 41) | GTCTGCGGGATGGAAGGGA(SEQ ID NO: 42) |
| UGT1A1 | CATGCTGGGAAGATACTGTTGAT(SEQ ID NO: 43) | GCCCGAGACTAACAAAAGACTCT(SEQ ID NO: 44) |
| GSTA1 | CTGCCCGTATGTCCACCTG(SEQ ID NO: 45) | AGCTCCTCGACGTAGTAGAGA(SEQ ID NO: 46) |
| APOC3 | GAAGCACGCCACCAAGAC(SEQ ID NO: 47) | CAGGGTCCAAATCCCAGAA(SEQ ID NO: 48) |
| UGT2B7 | AAGGTGCTGGTGTGGGCAG(SEQ ID NO: 49) | AGCGGATGAGTTGTTGGGA(SEQ ID NO: 50) |
| CYP2E1 | ATGTCTGCCCTCGGAGTCA(SEQ ID NO: 51) | CGATGATGGGAAGCGGGAAA(SEQ ID NO: 52) |
| CD44 | ACCATGGACAAGTTTTGGTG(SEQ ID NO: 53) | GAAAGCCTTGCAGAGGTCAG(SEQ ID NO: 54) |
| CK7 | GAAGCATGGGGACGACCT(SEQ ID NO: 55) | CACGAGCATCCTTGAGCG(SEQ ID NO: 56) |
| SCTR | AATCTGGCCTGTGGCGTTAAT(SEQ ID NO: 57) | GTAGTTGCGAGTGCAGTGGA(SEQ ID NO: 58) |
| SSTR2 | AACCAGACAGAGCCGTACTA(SEQ ID NO: 59) | GCATAGCGGAGGATGACATAAA(SEQ ID NO: 60) |
| AQP1 | TAACCCTGCTCGGTCCTTTG(SEQ ID NO: 61) | CCACCCTGGAGTTGATGTCG(SEQ ID NO: 62) |
| P21 | CTGGACTGGGCACTCTTGTC(SEQ ID NO: 63) | CTCCTACCATCCCCTTCCTC(SEQ ID NO: 64) |
| P53 | CCGCAGTCAGATCCTAGCG(SEQ ID NO: 65) | AATCATCCATTGCTTGGGACG(SEQ ID NO: 66) |

TABLE 3-continued

| Gene | Forward (5'-3') | Reverse (5'-3') |
|---|---|---|
| P14 | TACTGAGGAGCCAGCGTCTA(SEQ ID NO: 67) | TGCACGGGTCGGGTGAGAGT(SEQ ID NO: 68) |
| CXCL1 | AGTGGCACTGCTGCTCCT(SEQ ID NO: 69) | GGATTTGTCACTGTTCAGC(SEQ ID NO: 70) |

2.5 Human Albumin ELISA

ALB ELISA kit (Bethyl Laboratories) was used for the detection.

2.6 Urea Assay

For detecting urea secretion ability of the cultured cells, supernatants of cell culture were collected after 24-hour culture and analyzed by urea assay kit (Abnova) according to its protocol.

2.7 PAS Staining and Oil Red Staining

Cells were stained by PAS (Periodic Acid-Schiff) using Sigma's kit. For oil red staining of cells, the medium was removed and cells were washed with PBS. Cells were fixed for 30 minutes by adding 4% paraformaldehyde, and washed 3 times with PBS after paraformaldehyde was removed. Then cells were stained by Oil Red O (Sigma-Aldrich) for 10 min, and washed twice by 70% ethanol, followed by observing and photographing under a microscope.

2.8 Senescence-Related β-Galactosidase Staining

For senescence-associated β-galactosidase staining, the medium was removed and cells were washed with PBS. Cells were fixed with 4% paraformaldehyde for 5 minutes, and washed 3 times with PBS after paraformaldehyde was removed. Cells were stained by β-galactosidase Staining Kit (Beyotime) following instructions for use, and then observed and photographed under a microscope.

2.9 CYP2B6 Metabolism Assay

For measurement of CYP2B6 metabolism activity of the proliferating human hepatocytes, cells subjected 10 days of hepatic induction and freshly resuscitated human hepatocytes were incubated respectively in a medium containing 100 um bupropion. Supernatants of cell culture were present to RILD Liver Company to detect the production of CYP2B6 metabolites using mass spectrometry. Standard curves were drawn using commercially purchased standards.

2.10 RNA-Sequencing

RNA was extracted using Trizol (Invitrogen) according to its protocol. Sequencing library was prepared from one microgram of total RNA using Illumina TruSeq RNA Sample Prep Kit. Single-end 100 bp read length sequencing was performed on Illumina Hiseq 2000 sequencer. The reads were mapped to the human reference genome (hg19) using Tophat. FPKM (fragments per kilobase of exon per million fragments mapped) values for UCSC genes were calculated by Cufflinks using default parameters. The FPKM were Log 2 transformed for downstream analysis. For gene expression analysis, a one-way ANOVA was performed to identify differentially expressed genes (DEGs). P values and fold-change were calculated for each analysis. Unsupervised clustering and heatmap generation were performed with sorted or whole genes using the Euclidean distance of the average-linkage clustering of the selected probe sets based on Partek genomics suite 6.6.

2.11 Pathway Enrichment Analysis

Gene set enrichment analysis (GSEA) was used for pathway enrichment of DEGs. For the list of DEGs, online MSIGDB tool was used (http://Studio.org/gSe/MSigDb/index.jsp). GSEA v2 desktop software was also used to identify the significantly enriched pathways from the RNASEQ results.

2.12 Transplantation of cells into $Fah^{-/-}Rag2^{-/-}IL2rg^{-/-}$ mice

1) Six days before cells transplantation, NTBC in drinking water of mice was withdrawn to cause liver injury.
2) With the spleen side of the mouse facing up, cut the epidermis and muscle layer 1-2 cm below the ribs. Find the brown fat attached to the spleen and pull it out together with the spleen. Tie the front of the spleen gently with a thread.
3) Take $5*10^5$ proliHHs or human primary hepatocytes (about 100 ul) with insulin needles, and insert the needle into the spleen beyond the tied position. Hold the needle for 30-60 seconds after the injection, then pull out the needle and tie the thread tightly to prevent the liquid from flowing back.
4) Put the spleen back into the abdominal cavity, suture the muscle and epidermis, disinfect the wound with alcohol cotton, and put the mouse in the cage. The weight and survival were recorded weekly after transplantation. Mice without transplanted cells and having a 30% weight loss were used as negative controls.
5) Mice that survived to 12 weeks were processed and their liver and blood samples were collected for downstream analysis.

2.13 Subcutaneous Tumor Formation Assay

1) ProliHHs and hepatoma cell line Snu398 were digested, and $2*10^6$ cells were directly injected into the groin of immunodeficient NOD-SCID mice.
2) Tumor formation were assayed and photographed two months after injection.

2.14 Statistical Analysis

Statistic calculation was performed using GraphPad Prism 5. For survival analysis of rats after primary hepatocyte transplantation, the two-tailed log-rank test was applied. For the serological data statistic, an unpaired Student's T-test was applied. The data shown in Figures is mean±SD. * $P<0.05$, indicating a significant difference.

Figure 1:
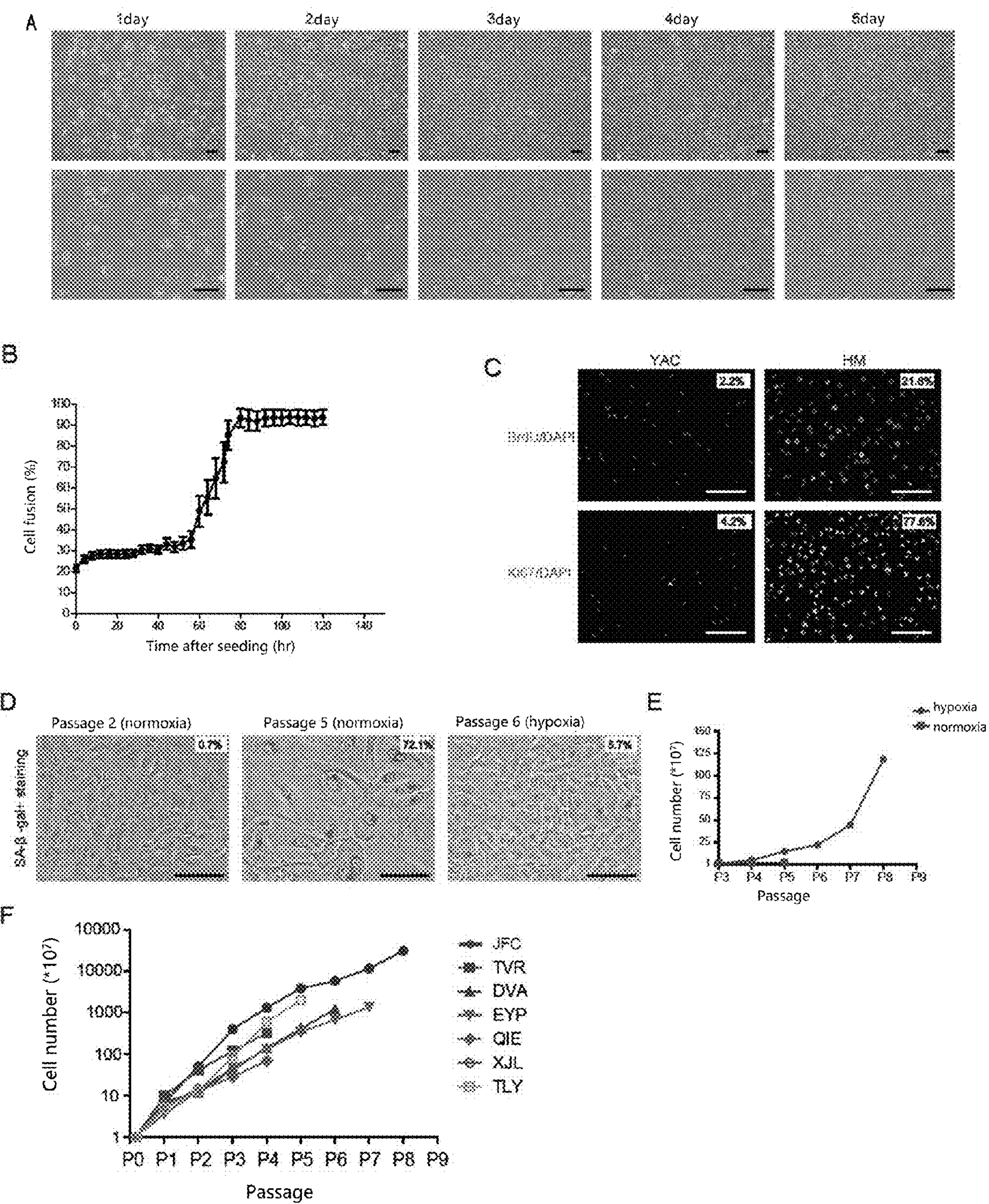
FIG. 1. When cultured in HM medium and under hypoxia condition, the long-term expansion of human hepatocytes in vitro was promoted.

Example 1. HM Medium Combined with Hypoxia can Promote the Long-Term Expansion of Human Hepatocytes In Vitro Through the selection and optimization of the medium components, the inventor obtained a medium that can promote the expansion of human hepatocytes in vitro, and named it HM medium. The human hepatocytes were plated on a 6-well plate at $1*10^5$ cells/well, and HM medium was added for culture. By real-time observation in the live cell workstation, it can be found that human hepatocytes undergo epithelial cell-mesenchymal transformation on the second day, followed by massive proliferation from the second day to the third day (FIGS. 1A and B). On day 3, it was found that 80% of the cells were Ki67 positive, and a BrdU incubation for 3 hr showed that 20% of the cells were at the replication phase (FIG. 1C). In YAC, a medium previously reported to induce the proliferation of mouse hepatocytes, human hepatocytes rarely proliferate and replicate (FIG. 1C).

The expanded human hepatocytes were serially passaged. Under normoxia (20%), hepatocytes stopped proliferating at the 5th passage and 72% of the cells were SA-β-gal positive, indicating the cessation of proliferation of human hepatocytes due to senescence (FIGS. 1D and E). The inventor unexpectedly discovered that, hypoxia (5% (v/v) significantly inhibited liver cell senescence and increased the passage number (FIGS. 1D and E). In addition, 7 different donor hepatocytes could be continuously expanded in HM medium combined with hypoxia, further confirming the generalizability of this culture method (FIG. 1F).

The above results prove that HM medium can promote the continuous proliferation of human hepatocytes in vitro; further combined with hypoxia treatment can promote this continuous proliferation in vitro.

Example 2. Wnt3a is Necessary for HM Medium to Promote Hepatocyte Proliferation The HM medium contains a variety of growth factors and small molecule compounds. The inventor has found that removal of Wnt3a conditioned medium prevented the proliferation of human hepatocytes (FIGS. 2A and B).

When Wnt3a conditioned medium was replaced by 50 ng/ml Wnt3a purified protein or Wnt signaling pathway agonist CHIR (0.1 μM), human hepatocytes could be expanded, and showed similar cell morphology and expansion fold (FIGS. 2A and B).

The above results prove that the Wnt signaling pathway agonist is critical in the HM medium for the proliferation of hepatocytes, and the Wnt signaling pathway agonist can be Wnt3a conditioned medium, an agonist protein or small molecule of the Wnt signaling pathway.

Example 3. The Proliferating Human Hepatocytes Maintain Some Function of Mature Hepatocytes Mature hepatocyte genes were expressed in HM-cultured human hepatocytes but at different levels from primary human hepatocytes (PHH, freshly resuscitated primary human hepatocytes, uncultured). ALB, HNF4A, TTR, and CYP3A4 were expressed at lower levels than those of PHHs, and CYP1A2, CAR, C3, and UGT1A1 were at similar levels or higher levels than those of PHHs (FIG. 3A). As validated by immunofluorescent staining, over 97% of proliferated human hepatocytes (ProliHHs) expressed mature hepatocyte marker proteins ALB and AAT (FIG. 3B). To analyze the level of the hepatocytes gene expression of ProliHHs, the inventor compared PHHs, ProliHHs and hepatocyte-like cells derived from embryonic stem cells by differentiation and from fibroblasts by transdifferentiation (HLCs; hepatocyte-like cells derived from embryonic stem cell by differentiation and from fibroblasts by transdifferentiation) for the difference in transcriptome. Principal-component analysis and cluster analysis revealed that ProliHHs were close to PHHs, but were far distinct from HLCs (FIG. 3C). This showed that ProliHHs were more mature than HLCs in terms of hepatocytes gene expression. According to Gene Set Enrichment Analysis (GSEA), ProliHHs showed more enrichment in expression of genes involved in drug, bile acid, fatty acid and urea metabolism signaling pathway than HLC (FIG. 3D). In line with the hepatic gene expression, ProliHHs maintained high levels of ALB secretion, glycogen storage and synthesis of lipid droplet (FIGS. 3E and F).

These results indicated that the proliferating human hepatocytes maintain some functions of mature hepatocytes.

Example 4. The Proliferating Human Hepatocytes are in the Intermediate-State Between Mature Hepatocytes and Liver Progenitor Cells HM-cultured human hepatocytes showed expression of liver progenitor cells-associated genes such as SOX9, EPCAM, CD44, CD133, CK19, and CK7 (FIG. 4A). Immunofluorescent staining further showed that more than 97% of ProliHHs expressed liver progenitor cell-associated markers SOX9, CK19 and CK7 (FIG. 4B). To analyze the similarity between ProliHHs and liver precursor cells (LPC; liver precursor cells obtained from human embryonic stem cells by in vitro differentiation), the inventor compared PHHs, ProliHHs and LPCs derived from embryonic stem cells by differentiation for the difference in transcriptome. When compared to PHHs, 3,482 genes were upregulated in LPCs (FIG. 4C), among which 1,652 (47.4%) were also upregulated in ProliHHs (FIG. 4C). This implies that ProliHHs has obtained the expression of a large number of liver precursor cell-enriched genes at the entire transcriptome level by the culture. Analysis of the differential gene expression profiles of PHHs, ProliHHs and LPCs revealed that the genes enriched in LPC can be divided into 3 sets (FIG. 4D). Based on the profiles of differential gene expression between PHHs, ProliHHs, and LPCs, the genes enriched in LPCs could be divided into three clusters (FIG. 4D). Genes in cluster 1 and 2 had lower expressions in PHHs, higher expressions in LPCs, and gradually upregulated expressions in ProliHHs as the culture progressed. Gene set enrichment analysis confirmed that genes in cluster 1 and 2 were enriched in several pathways relative to stem cells and cell cycles (FIG. 4E). The genes of cluster 3 had lower expressions in PHHs, higher expressions in LPCs, but no significantly upregulated expressions in ProliHHs as the culture progressed, such as the previously reported liver precursor genes DLK1, KIT, and FOXJ1, etc. (FIG. 4D) However, when analyzing the whole expression profiles, ProliHHs still presented expression profiles close to PHHs and were separated from LPCs (FIG. 4F). These results suggested that, although ProliHHs expressed a large portion of liver progenitor cell-associated genes during the culture, they did not establish the whole gene profile of liver progenitor cells.

Therefore, ProliHHs were at a bi-phenotypic intermediate-state between mature hepatocytes and liver progenitor cells.

Example 5. Proliferating Human Hepatocytes can be Induced into Mature Hepatocytes In Vitro Proliferating human hepatocytes down-regulated the expression of some mature liver genes and up-regulated the expression of liver progenitor-associated genes during in vitro expansion. To confirm whether they can be induced into mature hepatocytes in vitro, the inventor cultured ProliHHs in hepatic maturation medium (HIM) for 10 days in a three-dimensional culture (normoxia) (FIG. 5A). After maturation, ProliHHs formed typical polygonal shape and bi-nuclear of mature hepatocytes (FIG. 5B). In addition to the change in morphology, expression of hepatocyte genes, such as ALB, TTR, HNF4A and AAT, were significantly increased in ProliHHs, while the expression levels of liver progenitor genes, such as SOX9, CK19, and CK7, were largely reduced (FIG. 5C). More importantly, in concordance with up-regulated levels in key genes involved in drug and urea metabolism, the metabolic activity of CYP2B6 and urea were increased after maturation (FIGS. 5D-F).

These results suggest that the proliferating human hepatocytes can be induced into mature hepatocytes in the hepatic induction maturation system in vitro.

Example 6. Key Factors that Promote Metabolic Maturation and Inhibit the Expression of Progenitor Genes The expanded hepatocytes were placed in 3D culture conditions to form liver organoids, which were cultured with HM and HIM, respectively. Quantitative PCR was used to detect the expression of liver cell gene CYP3A4 (key metabolic gene) and liver progenitor genes SOX9, EPCAM, CD133, CK19, CK7.

The hepatic maturation medium (HIM) consisted of HM medium, Forskolin, DEX and OSM. After 3D sphere formation culture of the expanded hepatocytes, cells were cultured with HM and HIM. As shown in FIG. 6, gene expression analysis showed that expression of CYP3A4 in HIM-cultured liver organoids was significantly higher than that of HM-cultured liver organoids, while expression of liver progenitor genes such as CD133 and CK19 was lower in HIM-cultured liver organoids.

The above results prove that Forskolin, DEX and OSM are the key factors that promote the metabolic maturation of hepatocytes and inhibit the expression of progenitor genes in the hepatic maturation medium.

Example 7. The Proliferating Human Hepatocytes can be Used for Treatment of Liver Diseases by Cell Transplantation In order to prove that the proliferated human hepatocytes can be used for treatment of liver diseases by cell transplantation, the inventor transplanted them into $Fah^{-/-}Rag2^{-/-}IL2rg^{-/-}$ (FRG) mice. FRG mice are an immunodeficiency mice that mimic human tyrosinemia type I. FRG mice cannot survive unless they are supplied with 2-(2-nitro-4-trifluoro-methylbenzyol)-1,3-cyclohexanedione (NTBC) in drinking water. Withdrawal of NTBC will cause the mice die of liver failure within 4-6 weeks, and human primary hepatocytes can efficiently repopulated in FRG's liver and save them from liver failure. Therefore, FRG mice are a useful model for verifying the function of human hepatocytes in vivo.

Method of transplanting ProliHHs: six days before cells transplantation, NTBC in drinking water of mice was withdrawn to cause liver injury; $5\times10^5$ human primary hepatocytes PHHs and the expanded hepatocytes ProliHHs were intrasplenically transplanted into FRG mice.

After withdrawal of NTBC, 5 of the 6 FRG mice without transplantation died within 7 weeks, whereas 5 of the 7 FRG mice transplanted with human primary hepatocytes survived. Survival rate of mice was significantly improved (FIG. 7A). More importantly, 11 of the 14 FRG mice that transplanted with ProliHHs survived for more than 4 months. The ProliHH-transplanted mice lost body weight during the first 4 weeks after transplantation but later regained the body weight and remained stable (FIG. 7B). This suggests that transplanted ProliHHs can restore functions of the injured livers of FRG mice. Serological testing further confirmed the recovery of liver function. ALT, AST, and TBIL were significantly reduced in ProliHH-transplanted mice as compared to dying FRG mice without transplantation, and restored to levels comparable to those of PHH-transplanted mice (FIG. 7C). The secretion of human albumin in mouse serum increased gradually after transplantation of ProliHHs and reached the levels of 5.8±4.5 mg/mL at 4 months (FIGS. 7D and E). Such secretion levels were comparable to that of FRG mice transplanted with human primary hepatocytes (7.3±6.1 mg/ml, FIGS. 7D and E). Fah immunohistochemical staining of the liver samples of mice survived for 4 months showed that ProliHHs repopulated 64%±21.8% of the liver (FIGS. 7F and G). This repopulation capacity of ProliHHs in vivo was comparable to that of PHHs as shown by PHH-transplanted mice (70.4%±21.5%, FIGS. 7F and G).

The above results indicate that ProliHHs can efficiently repopulate the liver of FRG mice and has a therapeutic effect on liver injury.

Example 8. After Transplantation, the Liver Function of the Proliferating Human Hepatocytes is Fully Mature In Vivo The proliferating human hepatocytes ProliHHs up-regulated the expression of liver progenitor-associated genes during in vitro expansion. To reveal whether it can be induced into mature hepatocytes in vivo, the inventor analyzed and identified ProliHHs repopulated in the liver of FRG mice. Immunofluorescent staining showed that ProliHHs in vivo expressed mature hepatocyte markers ALB, FAH, HNF4A and CYP3A4, but did not express liver progenitor cell-associated genes CK19 and CK7 (FIGS. 8A and B). QPCR detection with human-specific liver gene primers showed that the expression of mature hepatocyte genes such as phase I and II metabolic enzymes and transporter proteins in ProliHHs in vivo was significantly higher than that in cultured ProliHHs in vitro (FIG. 8C). The overall transcriptome analysis showed that there was a high similarity between in vivo ProliHHs and PHHs ($r^2$=0.94), indicating that the expression of hepatocyte genes in ProliHHs in vivo is close to that in PHHs (FIG. 8D).

In order to prove that ProliHHs transplanted into the body has metabolism function of mature hepatocytes, the inventor assayed the humancCYP2D6-specific drug metabolism in transplanted mice. As a metabolic substrate of human CYP2D6, debrisoquine (DEB) cannot be metabolized by mouse hepatocytes, but can only be metabolized to 4-hydroxyisoquinoline (4-OH-DEB) by human hepatocytes. After oral administration of DEB, FRG mice transplanted with ProliHHs showed higher amounts of 4-OH DEB in serum (FIG. 8E). Amounts of 4-OH-DEB of the non-transplanted FRG mice in the control group were still at the background level (FIG. 8E). These data suggested that ProliHHs is fully mature with human-specific drug metabolism ability in vivo.

The above results show that the proliferating human hepatocytes can be induced into mature hepatocytes following massive repopulations in the liver.

Example 9. The Proliferating Human Hepatocytes do not have a Risk of Tumorigenesis In Vivo Proliferating human hepatocytes have the ability to continuously expand after being cultured in vitro. In order to find out whether the expanded ProliHHs has the risk of tumorigenesis in vivo, the inventor injected $2\times10^6$ ProliHHs and liver cancer cell line Snu-398 subcutaneously in NOD-SCID mice with severe immunodeficiency. Two months later, all the 6 mice injected with Snu-398 had tumors, while the 8 mice injected with ProliHHs did not form a tumor (FIG. 9).

The above results indicate that the proliferated human hepatocytes have no risk of tumorigenesis in vivo.

Example 10. In Vitro Expansion with HM2, HM3 and HIM2, HIM3

In order to validate the effect of HM medium, the inventor prepared in vitro expansion medium HM2 and HM3 and hepatic maturation medium HIM2 and HIM3, as shown in Table 4 and Table 5.

TABLE 4

| | HM2 | HM3 |
|---|---|---|
| Advanced DMEM/F-12 | 1X | 1X |
| N2 supplement 100x | 1X | 1X |
| B27 ™ Supplement 50x, minus vitamin A | 1X | 1X |
| N-acetylcysteine | 0.8 mM | 1.2 mM |
| Nicotinamide | 12 mM | 8 mM |
| Recombinant human FGF10 | 1.6 ng/ml | 2.5 ng/ml |
| Recombinant human EGF | 60 ng/ml | 40 ng/ml |
| Recombinant human HGF | 20 ng/ml | 30 ng/ml |
| Human [Leu15]-gastrin I | 12 mM | 8 mM |
| A 83-01 | 4 uM | 6 uM |
| Rho kinase inhibitor Y-27632 | 12 uM | 8 uM |
| Wnt3a Protein | 40 ng/ml | 60 ng/ml |
| Bovine Serum | 1.2% | 0.8% |
| Penicillin Streptomycin | 1X | 1X |

TABLE 5

| | HIM2 | HIM3 |
|---|---|---|
| Advanced DMEM/F-12 | 1X | 1X |
| N2 supplement 100x | 1X | lX |
| B27 ™ Supplement 50x, minus vitamin A | 1X | 1X |
| N-acetylcysteine | 0.8 mM | 1.2 mM |
| Nicotinamide | 12 mM | 8 mM |
| Recombinant human FGF10 | 1.6 ng/ml | 2.5 ng/ml |
| Recombinant human EGF | 60 ng/ml | 40 ng/ml |
| Recombinant human HGF | 20 ng/ml | 30 ng/ml |
| Human [Leu15]-gastrin I | 12 mM | 8 mM |
| A 83-01 | 4 uM | 6 uM |
| Rho kinase inhibitor Y-27632 | 12 uM | 8 uM |
| Wnt3a Protein | 40 ng/ml | 60 ng/ml |
| Forskolin | 4 uM | 7 uM |
| Dexamethasone(DEX) | 13 μM | 8 uM |

TABLE 5-continued

| | HIM2 | HIM3 |
|---|---|---|
| Oncostatin M(OSM) | 17 ng/ml | 25 ng/ml |
| Bovine Serum | 1.2% | 0.8% |
| Penicillin Streptomycin | 1% | 1% |

The normoxic culture was performed as in Example 1 with human primary hepatocytes as initial cells, except that the HM medium in Example 1 was replaced with HM2. The results showed that under normoxic conditions, human hepatocytes underwent epithelial-to-mesenchymal transition on the second day, followed by massive proliferation from the second to the third day; and the proliferating human hepatocytes is in an intermediate-state between mature hepatocytes and liver progenitor cells.

The normoxic culture was performed as in Example 1 with human primary hepatocytes as initial cells, except that the HM medium in Example 1 was replaced with HM3, and the hypoxic condition was 7% oxygen. The results showed that under hypoxic conditions, human hepatocytes proliferated in large quantities; and the proliferating human hepatocytes were in an intermediate-state between mature hepatocytes and liver progenitor cells, and passage number can be more than 6.

The culture was performed as in Example 5 with ProliHHs as initial cells, except that the HIM medium in Example 5 was replaced with HIM2. The results showed that after induced maturation, ProliHHs had the typical polygonal shape and bi-nuclear of mature hepatocytes; hepatocyte genes such as ALB, TTR, HNF4A and AAT were also significantly up-regulated, while liver progenitor genes such as SOX9, CK19 and CK7 were significantly down-regulated.

The culture was performed as in Example 5 with ProliHHs as initial cells, except that the HIM medium in Example 5 was replaced with HIM3. The results showed that after induced maturation, ProliHHs had the typical polygonal shape and bi-nuclear of mature hepatocytes; hepatocyte genes such as ALB, TTR, HNF4A and AAT were also significantly up-regulated, while liver progenitor genes such as SOX9, CK19 and CK7 were significantly down-regulated.

Each reference provided herein is incorporated by reference to the same extent as if each reference was individually incorporated by reference. In addition, it should be understood that based on the above teaching content of the disclosure, those skilled in the art can practice various changes or modifications to the disclosure, and these equivalent forms also fall within the scope of the appended claims.

We claim:

1. A method for in vitro hepatocyte expansion, comprising culturing hepatocytes in a cell culture medium to expand the hepatocytes in vitro, wherein said cell culture medium consists of a basal medium and a Wnt signaling pathway agonist, N-acetylcysteine, nicotinamide, recombinant human FGF10, recombinant human EGF, recombinant human HGF, human [Leu$^{15}$]-gastrin I, A 83-01, Y-27632, serum, N2 supplement and neuronal culture supplement; wherein said Wnt signaling pathway agonist is selected from Wnt3a protein or CHIR; wherein the concentration of each component is

| | |
|---|---|
| Wnt3a protein | 30 to 70 ng/ml, or |
| CHIR | 0.05 to 2 μM; |
| N-acetylcysteine | 0.5 to 2 mM; |
| nicotinamide | 5 to 20 mM; |
| recombinant human FGF10 | 1 to 4 ng/ml; |
| recombinant human EGF | 30 to 70 ng/ml; |
| recombinant human HGF | 15 to 40 ng/ml; |
| human [Leu$^{15}$]-gastrin I | 5 to 20 mM; |
| A 83-01 | 3 to 7 μM ; |
| Y-27632 | 5 to 20 μM; and |
| serum | 0.5 to 2%, and |

wherein the hepatocytes are human hepatocytes.

2. The method according to claim 1, wherein said basal medium is selected from the group consisting of DMEM, MEM, RPMI, Neuronal basal and Fischers.

3. The method according to claim 1, wherein the method further comprises inducing the expanded hepatocytes into mature hepatocytes, including adding forskolin, dexamethasone, and oncostatin M to the cell culture medium, wherein concentrations of forskolin, dexamethasone, and oncostatin M in the cell culture medium are as follows forskolin 3 to 7 μM;

dexamethasone 5 to 20 μM; and oncostatin M 10 to 30 ng/ml.

4. The method according to claim 1, wherein the method further comprises sub-culturing the expanded hepatocytes under hypoxic conditions, wherein the hypoxic conditions contain 1-10% oxygen by volume, and wherein the sub-culture is a three-dimensional culture to form organoids.

5. The method according to claim 1, wherein the expanded hepatocytes are between mature hepatocytes and liver progenitor cells, and characterized by expressing liver progenitor cell-associated markers SOX9, CK19 and CK7, presenting lower expression levels of ALB, HNF4A, TTR or CYP3A4 compared to hepatocyte not cultured in the medium of claim 1 hepatocytes, and presenting similar or higher expression levels of CYP1A2, CAR, C3 or UGT1A1 compared to hepatocyte not cultured in the medium of claim 1 hepatocytes.

6. A method for in vitro hepatocyte expansion, comprising culturing hepatocytes in a cell culture medium to expand the hepatocytes in vitro, wherein said cell culture medium consists of a basal medium and a Wnt signaling pathway agonist, N-acetylcysteine, nicotinamide, recombinant human FGF10, recombinant human EGF, recombinant human HGF, human [Leu$^{15}$]-gastrin I, A 83-01, Y-27632, serum, N2 supplement and neuronal culture supplement; wherein said Wnt signaling pathway agonist is selected from Wnt3a protein or CHIR; wherein the concentration of each component is

| | |
|---|---|
| Wnt3a protein | 30 to 70 ng/ml, or |
| CHIR | 0.05 to 2 μM; |
| N-acetylcysteine | 0.5 to 2 mM; |
| nicotinamide | 5 to 20 mM; |
| recombinant human FGF10 | 1 to 4 ng/ml; |
| recombinant human EGF | 30 to 70 ng/ml; |
| recombinant human HGF | 15 to 40 ng/ml; |

-continued

| | |
|---|---|
| human [Leu$^{15}$]-gastrin I | 5 to 20 mM; |
| A 83-01 | 3 to 7 μM ; |
| Y-27632 | 5 to 20 μM; and |
| serum | 0.5 to 2%, and |

wherein the hepatocytes are human hepatocytes.

* * * * *

SEQUENCE LISTING

```
<160> NUMBER OF SEQ ID NOS: 70

<210> SEQ ID NO 1
<211> LENGTH: 18
<212> TYPE: DNA
<213> ORGANISM: Artificial
<220> FEATURE:
<223> OTHER INFORMATION: primer

<400> SEQUENCE: 1

gcctttgctc agtatctt                                                18


<210> SEQ ID NO 2
<211> LENGTH: 18
<212> TYPE: DNA
```

<213> ORGANISM: Artificial
<220> FEATURE:
<223> OTHER INFORMATION: primer

<400> SEQUENCE: 2
aggtttgggt tgtcatct 18

<210> SEQ ID NO 3
<211> LENGTH: 19
<212> TYPE: DNA
<213> ORGANISM: Artificial
<220> FEATURE:
<223> OTHER INFORMATION: primer

<400> SEQUENCE: 3
tatgatgaag cgtttaggc 19

<210> SEQ ID NO 4
<211> LENGTH: 20
<212> TYPE: DNA
<213> ORGANISM: Artificial
<220> FEATURE:
<223> OTHER INFORMATION: primer

<400> SEQUENCE: 4
cagtaatgga cagtttgggt 20

<210> SEQ ID NO 5
<211> LENGTH: 19
<212> TYPE: DNA
<213> ORGANISM: Artificial
<220> FEATURE:
<223> OTHER INFORMATION: primer

<400> SEQUENCE: 5
tgggagccat ttgcctctg 19

<210> SEQ ID NO 6
<211> LENGTH: 21
<212> TYPE: DNA
<213> ORGANISM: Artificial
<220> FEATURE:
<223> OTHER INFORMATION: primer

<400> SEQUENCE: 6
agccgtggtg gaataggagt a 21

<210> SEQ ID NO 7
<211> LENGTH: 20
<212> TYPE: DNA
<213> ORGANISM: Artificial
<220> FEATURE:
<223> OTHER INFORMATION: primer

<400> SEQUENCE: 7
cttcgctacc tgcctaaccc 20

<210> SEQ ID NO 8
<211> LENGTH: 21
<212> TYPE: DNA
<213> ORGANISM: Artificial
<220> FEATURE:
<223> OTHER INFORMATION: primer

<400> SEQUENCE: 8
gactgtgtca aatcctgctc c 21

<210> SEQ ID NO 9
<211> LENGTH: 18
<212> TYPE: DNA
<213> ORGANISM: Artificial
<220> FEATURE:
<223> OTHER INFORMATION: primer

<400> SEQUENCE: 9
cagcacttcc tgaatgag 18

<210> SEQ ID NO 10
<211> LENGTH: 23
<212> TYPE: DNA
<213> ORGANISM: Artificial
<220> FEATURE:
<223> OTHER INFORMATION: primer

<400> SEQUENCE: 10
aggtgactgg gaggacttga ggc 23

<210> SEQ ID NO 11
<211> LENGTH: 21
<212> TYPE: DNA
<213> ORGANISM: Artificial
<220> FEATURE:
<223> OTHER INFORMATION: primer

<400> SEQUENCE: 11
gcactcctca caggactctt g 21

<210> SEQ ID NO 12
<211> LENGTH: 20
<212> TYPE: DNA
<213> ORGANISM: Artificial
<220> FEATURE:
<223> OTHER INFORMATION: primer

<400> SEQUENCE: 12
cccaggtgta ccgtgaagac 20

<210> SEQ ID NO 13
<211> LENGTH: 24
<212> TYPE: DNA
<213> ORGANISM: Artificial
<220> FEATURE:
<223> OTHER INFORMATION: primer

<400> SEQUENCE: 13
tgaaggatga ggccgtctgg gaga 24

<210> SEQ ID NO 14
<211> LENGTH: 24
<212> TYPE: DNA
<213> ORGANISM: Artificial
<220> FEATURE:
<223> OTHER INFORMATION: primer

<400> SEQUENCE: 14
cagtgggcac cgagaagctg aagt 24

<210> SEQ ID NO 15
<211> LENGTH: 23
<212> TYPE: DNA
<213> ORGANISM: Artificial
<220> FEATURE:

<223> OTHER INFORMATION: primer

<400> SEQUENCE: 15
ttcagcaaga agaacaagga caa 23

<210> SEQ ID NO 16
<211> LENGTH: 22
<212> TYPE: DNA
<213> ORGANISM: Artificial
<220> FEATURE:
<223> OTHER INFORMATION: primer

<400> SEQUENCE: 16
ggttgaagaa gtcctcctaa gc 22

<210> SEQ ID NO 17
<211> LENGTH: 21
<212> TYPE: DNA
<213> ORGANISM: Artificial
<220> FEATURE:
<223> OTHER INFORMATION: primer

<400> SEQUENCE: 17
agaagcattg acccgatgga t 21

<210> SEQ ID NO 18
<211> LENGTH: 21
<212> TYPE: DNA
<213> ORGANISM: Artificial
<220> FEATURE:
<223> OTHER INFORMATION: primer

<400> SEQUENCE: 18
agcggtcttt gagttagagg a 21

<210> SEQ ID NO 19
<211> LENGTH: 19
<212> TYPE: DNA
<213> ORGANISM: Artificial
<220> FEATURE:
<223> OTHER INFORMATION: primer

<400> SEQUENCE: 19
gtgctcctgt gcggagtag 19

<210> SEQ ID NO 20
<211> LENGTH: 21
<212> TYPE: DNA
<213> ORGANISM: Artificial
<220> FEATURE:
<223> OTHER INFORMATION: primer

<400> SEQUENCE: 20
atggcagata ggcagtttcc c 21

<210> SEQ ID NO 21
<211> LENGTH: 19
<212> TYPE: DNA
<213> ORGANISM: Artificial
<220> FEATURE:
<223> OTHER INFORMATION: primer

<400> SEQUENCE: 21
aagcccagtg tcaacgcag 19

<210> SEQ ID NO 22
<211> LENGTH: 19
<212> TYPE: DNA
<213> ORGANISM: Artificial
<220> FEATURE:
<223> OTHER INFORMATION: primer

<400> SEQUENCE: 22
gggtcttccg ggtgatctc 19

<210> SEQ ID NO 23
<211> LENGTH: 22
<212> TYPE: DNA
<213> ORGANISM: Artificial
<220> FEATURE:
<223> OTHER INFORMATION: primer

<400> SEQUENCE: 23
aaccatactc gcaatacagc aa 22

<210> SEQ ID NO 24
<211> LENGTH: 21
<212> TYPE: DNA
<213> ORGANISM: Artificial
<220> FEATURE:
<223> OTHER INFORMATION: primer

<400> SEQUENCE: 24
acagctcatc ccctttgatc c 21

<210> SEQ ID NO 25
<211> LENGTH: 20
<212> TYPE: DNA
<213> ORGANISM: Artificial
<220> FEATURE:
<223> OTHER INFORMATION: primer

<400> SEQUENCE: 25
cagctgattg aggtgtccag 20

<210> SEQ ID NO 26
<211> LENGTH: 20
<212> TYPE: DNA
<213> ORGANISM: Artificial
<220> FEATURE:
<223> OTHER INFORMATION: primer

<400> SEQUENCE: 26
cactggagga tgtgagtgga 20

<210> SEQ ID NO 27
<211> LENGTH: 19
<212> TYPE: DNA
<213> ORGANISM: Artificial
<220> FEATURE:
<223> OTHER INFORMATION: primer

<400> SEQUENCE: 27
cctacggcgt cttctcgac 19

<210> SEQ ID NO 28
<211> LENGTH: 20
<212> TYPE: DNA
<213> ORGANISM: Artificial
<220> FEATURE:
<223> OTHER INFORMATION: primer

<400> SEQUENCE: 28
ctgcaagaac actctcgcct 20

<210> SEQ ID NO 29
<211> LENGTH: 20
<212> TYPE: DNA
<213> ORGANISM: Artificial
<220> FEATURE:
<223> OTHER INFORMATION: primer

<400> SEQUENCE: 29
actgaatcca gaacactgca 20

<210> SEQ ID NO 30
<211> LENGTH: 20
<212> TYPE: DNA
<213> ORGANISM: Artificial
<220> FEATURE:
<223> OTHER INFORMATION: primer

<400> SEQUENCE: 30
tgcagtcaat gcatctttca 20

<210> SEQ ID NO 31
<211> LENGTH: 17
<212> TYPE: DNA
<213> ORGANISM: Artificial
<220> FEATURE:
<223> OTHER INFORMATION: primer

<400> SEQUENCE: 31
ccacctttga cgctggg 17

<210> SEQ ID NO 32
<211> LENGTH: 23
<212> TYPE: DNA
<213> ORGANISM: Artificial
<220> FEATURE:
<223> OTHER INFORMATION: primer

<400> SEQUENCE: 32
cataccagga aatgagcttg aca 23

<210> SEQ ID NO 33
<211> LENGTH: 18
<212> TYPE: DNA
<213> ORGANISM: Artificial
<220> FEATURE:
<223> OTHER INFORMATION: primer

<400> SEQUENCE: 33
aggagatggg tgagatgc 18

<210> SEQ ID NO 34
<211> LENGTH: 19
<212> TYPE: DNA
<213> ORGANISM: Artificial
<220> FEATURE:
<223> OTHER INFORMATION: primer

<400> SEQUENCE: 34
gattggtaaa gccagtttc 19

<210> SEQ ID NO 35
<211> LENGTH: 19

<212> TYPE: DNA
<213> ORGANISM: Artificial
<220> FEATURE:
<223> OTHER INFORMATION: primer

<400> SEQUENCE: 35
tccactttgc catccctaa 19

<210> SEQ ID NO 36
<211> LENGTH: 20
<212> TYPE: DNA
<213> ORGANISM: Artificial
<220> FEATURE:
<223> OTHER INFORMATION: primer

<400> SEQUENCE: 36
ggtcgtccat actgctgttg 20

<210> SEQ ID NO 37
<211> LENGTH: 18
<212> TYPE: DNA
<213> ORGANISM: Artificial
<220> FEATURE:
<223> OTHER INFORMATION: primer

<400> SEQUENCE: 37
tgaaactgac tcggaagg 18

<210> SEQ ID NO 38
<211> LENGTH: 18
<212> TYPE: DNA
<213> ORGANISM: Artificial
<220> FEATURE:
<223> OTHER INFORMATION: primer

<400> SEQUENCE: 38
cagaatgaga tggtggtg 18

<210> SEQ ID NO 39
<211> LENGTH: 20
<212> TYPE: DNA
<213> ORGANISM: Artificial
<220> FEATURE:
<223> OTHER INFORMATION: primer

<400> SEQUENCE: 39
tccgaaccaa gtttgagacg 20

<210> SEQ ID NO 40
<211> LENGTH: 21
<212> TYPE: DNA
<213> ORGANISM: Artificial
<220> FEATURE:
<223> OTHER INFORMATION: primer

<400> SEQUENCE: 40
ccctcagcgt actgatttcc t 21

<210> SEQ ID NO 41
<211> LENGTH: 24
<212> TYPE: DNA
<213> ORGANISM: Artificial
<220> FEATURE:
<223> OTHER INFORMATION: primer

<400> SEQUENCE: 41
gactacaccg accaccagaa ctcc 24

<210> SEQ ID NO 42
<211> LENGTH: 19
<212> TYPE: DNA
<213> ORGANISM: Artificial
<220> FEATURE:
<223> OTHER INFORMATION: primer

<400> SEQUENCE: 42
gtctgcggga tggaaggga 19

<210> SEQ ID NO 43
<211> LENGTH: 23
<212> TYPE: DNA
<213> ORGANISM: Artificial
<220> FEATURE:
<223> OTHER INFORMATION: primer

<400> SEQUENCE: 43
catgctggga agatactgtt gat 23

<210> SEQ ID NO 44
<211> LENGTH: 23
<212> TYPE: DNA
<213> ORGANISM: Artificial
<220> FEATURE:
<223> OTHER INFORMATION: primer

<400> SEQUENCE: 44
gcccgagact aacaaaagac tct 23

<210> SEQ ID NO 45
<211> LENGTH: 19
<212> TYPE: DNA
<213> ORGANISM: Artificial
<220> FEATURE:
<223> OTHER INFORMATION: primer

<400> SEQUENCE: 45
ctgcccgtat gtccacctg 19

<210> SEQ ID NO 46
<211> LENGTH: 21
<212> TYPE: DNA
<213> ORGANISM: Artificial
<220> FEATURE:
<223> OTHER INFORMATION: primer

<400> SEQUENCE: 46
agctcctcga cgtagtagag a 21

<210> SEQ ID NO 47
<211> LENGTH: 18
<212> TYPE: DNA
<213> ORGANISM: Artificial
<220> FEATURE:
<223> OTHER INFORMATION: primer

<400> SEQUENCE: 47
gaagcacgcc accaagac 18

<210> SEQ ID NO 48
<211> LENGTH: 19
<212> TYPE: DNA
<213> ORGANISM: Artificial

<220> FEATURE:
<223> OTHER INFORMATION: primer

<400> SEQUENCE: 48
cagggtccaa atcccagaa 19

<210> SEQ ID NO 49
<211> LENGTH: 19
<212> TYPE: DNA
<213> ORGANISM: Artificial
<220> FEATURE:
<223> OTHER INFORMATION: primer

<400> SEQUENCE: 49
aaggtgctgg tgtgggcag 19

<210> SEQ ID NO 50
<211> LENGTH: 19
<212> TYPE: DNA
<213> ORGANISM: Artificial
<220> FEATURE:
<223> OTHER INFORMATION: primer

<400> SEQUENCE: 50
agcggatgag ttgttggga 19

<210> SEQ ID NO 51
<211> LENGTH: 19
<212> TYPE: DNA
<213> ORGANISM: Artificial
<220> FEATURE:
<223> OTHER INFORMATION: primer

<400> SEQUENCE: 51
atgtctgccc tcggagtca 19

<210> SEQ ID NO 52
<211> LENGTH: 20
<212> TYPE: DNA
<213> ORGANISM: Artificial
<220> FEATURE:
<223> OTHER INFORMATION: primer

<400> SEQUENCE: 52
cgatgatggg aagcgggaaa 20

<210> SEQ ID NO 53
<211> LENGTH: 20
<212> TYPE: DNA
<213> ORGANISM: Artificial
<220> FEATURE:
<223> OTHER INFORMATION: primer

<400> SEQUENCE: 53
accatggaca agttttggtg 20

<210> SEQ ID NO 54
<211> LENGTH: 20
<212> TYPE: DNA
<213> ORGANISM: Artificial
<220> FEATURE:
<223> OTHER INFORMATION: primer

<400> SEQUENCE: 54
gaaagccttg cagaggtcag 20

<210> SEQ ID NO 55
<211> LENGTH: 18
<212> TYPE: DNA
<213> ORGANISM: Artificial
<220> FEATURE:
<223> OTHER INFORMATION: primer

<400> SEQUENCE: 55
gaagcatggg gacgacct 18

<210> SEQ ID NO 56
<211> LENGTH: 18
<212> TYPE: DNA
<213> ORGANISM: Artificial
<220> FEATURE:
<223> OTHER INFORMATION: primer

<400> SEQUENCE: 56
cacgagcatc cttgagcg 18

<210> SEQ ID NO 57
<211> LENGTH: 21
<212> TYPE: DNA
<213> ORGANISM: Artificial
<220> FEATURE:
<223> OTHER INFORMATION: primer

<400> SEQUENCE: 57
aatctggcct gtggcgttaa t 21

<210> SEQ ID NO 58
<211> LENGTH: 20
<212> TYPE: DNA
<213> ORGANISM: Artificial
<220> FEATURE:
<223> OTHER INFORMATION: primer

<400> SEQUENCE: 58
gtagttgcga gtgcagtgga 20

<210> SEQ ID NO 59
<211> LENGTH: 20
<212> TYPE: DNA
<213> ORGANISM: Artificial
<220> FEATURE:
<223> OTHER INFORMATION: primer

<400> SEQUENCE: 59
aaccagacag agccgtacta 20

<210> SEQ ID NO 60
<211> LENGTH: 22
<212> TYPE: DNA
<213> ORGANISM: Artificial
<220> FEATURE:
<223> OTHER INFORMATION: primer

<400> SEQUENCE: 60
gcatagcgga ggatgacata aa 22

<210> SEQ ID NO 61
<211> LENGTH: 20
<212> TYPE: DNA
<213> ORGANISM: Artificial
<220> FEATURE:
<223> OTHER INFORMATION: primer

<400> SEQUENCE: 61
taaccctgct cggtcctttg 20

<210> SEQ ID NO 62
<211> LENGTH: 20
<212> TYPE: DNA
<213> ORGANISM: Artificial
<220> FEATURE:
<223> OTHER INFORMATION: primer

<400> SEQUENCE: 62
ccaccctgga gttgatgtcg 20

<210> SEQ ID NO 63
<211> LENGTH: 20
<212> TYPE: DNA
<213> ORGANISM: Artificial
<220> FEATURE:
<223> OTHER INFORMATION: primer

<400> SEQUENCE: 63
ctggactggg cactcttgtc 20

<210> SEQ ID NO 64
<211> LENGTH: 20
<212> TYPE: DNA
<213> ORGANISM: Artificial
<220> FEATURE:
<223> OTHER INFORMATION: primer

<400> SEQUENCE: 64
ctcctaccat ccccttcctc 20

<210> SEQ ID NO 65
<211> LENGTH: 19
<212> TYPE: DNA
<213> ORGANISM: Artificial
<220> FEATURE:
<223> OTHER INFORMATION: primer

<400> SEQUENCE: 65
ccgcagtcag atcctagcg 19

<210> SEQ ID NO 66
<211> LENGTH: 21
<212> TYPE: DNA
<213> ORGANISM: Artificial
<220> FEATURE:
<223> OTHER INFORMATION: primer

<400> SEQUENCE: 66
aatcatccat tgcttgggac g 21

<210> SEQ ID NO 67
<211> LENGTH: 20
<212> TYPE: DNA
<213> ORGANISM: Artificial
<220> FEATURE:
<223> OTHER INFORMATION: primer

<400> SEQUENCE: 67
tactgaggag ccagcgtcta 20

<210> SEQ ID NO 68

-continued

```
<211> LENGTH: 20
<212> TYPE: DNA
<213> ORGANISM: Artificial
<220> FEATURE:
<223> OTHER INFORMATION: primer

<400> SEQUENCE: 68

tgcacgggtc gggtgagagt                                                  20


<210> SEQ ID NO 69
<211> LENGTH: 18
<212> TYPE: DNA
<213> ORGANISM: Artificial
<220> FEATURE:
<223> OTHER INFORMATION: primer

<400> SEQUENCE: 69

agtggcactg ctgctcct                                                    18


<210> SEQ ID NO 70
<211> LENGTH: 19
<212> TYPE: DNA
<213> ORGANISM: Artificial
<220> FEATURE:
<223> OTHER INFORMATION: primer

<400> SEQUENCE: 70

ggatttgtca ctgttcagc                                                   19
```